US012788720B2

(12) United States Patent
Miller et al.

(10) Patent No.: US 12,788,720 B2
(45) Date of Patent: Nov. 10, 2026

(54) MIXED SOLVENTS FOR SPRAY DRYING FOR PREPARATION OF AMORPHOUS SOLID DISPERSIONS

(71) Applicant: Lonza Bend Inc., Bend, OR (US)

(72) Inventors: Warren Miller, Bend, OR (US); Molly Adam, Bend, OR (US); Michael Morgen, Bend, OR (US); John Baumann, Bend, OR (US)

(73) Assignee: Lonza Bend Inc., Bend, OR (US)

( * ) Notice: Subject to any disclaimer, the term of this patent is extended or adjusted under 35 U.S.C. 154(b) by 368 days.

(21) Appl. No.: 18/567,732

(22) PCT Filed: Jun. 8, 2022

(86) PCT No.: PCT/EP2022/065542

§ 371 (c)(1),
(2) Date: Dec. 6, 2023

(87) PCT Pub. No.: WO2022/258684

PCT Pub. Date: Dec. 15, 2022

(65) Prior Publication Data

US 2024/0277620 A1 Aug. 22, 2024

Related U.S. Application Data

(60) Provisional application No. 63/209,468, filed on Jun. 11, 2021, provisional application No. 63/208,643, filed on Jun. 9, 2021.

(30) Foreign Application Priority Data

Jun. 15, 2021 (EP) .................................... 21179384

(51) Int. Cl.

| | |
|---|---|
| ***A61K 9/16*** | (2006.01) |
| ***A61K 31/506*** | (2006.01) |
| ***A61K 31/5377*** | (2006.01) |
| ***A61K 31/655*** | (2006.01) |

(52) U.S. Cl.

CPC .......... *A61K 9/1694* (2013.01); *A61K 9/1635* (2013.01); *A61K 9/1652* (2013.01); *A61K 31/506* (2013.01); *A61K 31/5377* (2013.01); *A61K 31/655* (2013.01)

(58) Field of Classification Search

None

See application file for complete search history.

(56) References Cited

U.S. PATENT DOCUMENTS

| | | | |
|---|---|---|---|
| 5,648,096 | A | 7/1997 | Gander et al. |
| 7,235,259 | B2 | 6/2007 | Crew et al. |
| 8,034,381 | B2 | 10/2011 | Möschwitzer et al. |
| 8,216,495 | B2 | 7/2012 | Janssens et al. |
| 8,282,990 | B2 | 10/2012 | Kwak et al. |
| 8,372,836 | B2 | 2/2013 | Ketner et al. |
| 8,431,159 | B2 | 4/2013 | Curatolo et al. |
| 8,691,277 | B2 | 4/2014 | Zhang |
| 8,734,830 | B2 | 5/2014 | Hwang et al. |
| 8,771,739 | B2 | 7/2014 | Hayes et al. |
| 8,828,421 | B2 | 9/2014 | Drouillard et al. |
| 9,061,011 | B1 | 6/2015 | Voudouris |
| 9,248,101 | B2 | 2/2016 | Möschwitzer et al. |
| 9,248,584 | B2 | 2/2016 | Friesen et al. |

(Continued)

FOREIGN PATENT DOCUMENTS

| | | |
|---|---|---|
| CN | 110 037 990 A | 7/2019 |
| EP | 2 471 385 A1 | 7/2012 |

(Continued)

OTHER PUBLICATIONS

Hongwei Shi; Solubility enhancement, solvent effect and thermodynamic analysis of pazopanib in co-solvent mixtures https://doi.org/10.1016/j.jct.2020.106343 (Year: 2021).*

Ashland, "AquaSolve™ Hypromellose Acetate Succinate (HPMCAS) Versatile Pharmaceutical Polymers for Improved Solubility," Jun. 13, 2017, 4 pages.

Ashland, "AquaSolve™ Hypromellose Acetate Succinate Physical and Chemical Properties Handbook," Feb. 12, 2020, 16 pages.

(Continued)

*Primary Examiner* — Robert A Wax

*Assistant Examiner* — Andre Mach

(74) *Attorney, Agent, or Firm* — Klarquist Sparkman, LLP

(57) ABSTRACT

A method for preparing an amorphous solid dispersion by spray drying a spray solution comprising a) a mixed solvent, the mixed solvent comprising i. a solvent 1 selected from the group consisting of methyl acetate, methyl formate, ethyl acetate, ethyl formate and mixtures thereof; ii. a solvent 2 selected from the group consisting of methanol, ethanol and mixtures thereof; with the ratio (w:w) of solvent 1 to solvent 2 being from 10:90 to 90:10; b) an active agent; c) a dispersion polymer, wherein: c1) said dispersion polymer is HPMC; or c2) said dispersion polymer is PVP, provided that said mixed solvent does not consist of a mixture of methanol and ethyl acetate; or c3) said dispersion polymer is selected from the group consisting of: hydroxypropyl methylcellulose acetate succinate (HPMCAS), hydroxypropyl methylcellulose phthalate (HPMCP), hydroxypropyl cellulose (HPC), cellulose acetate phthalate (CAP), carboxymethyl ethyl cellulose (CMEC), poly(vinylpyrrolidone-co-vinyl acetate) (PVPVA), polymethacrylates such as poly(methacrylic acid-co-methyl methacrylate) (PMMAMA) or poly (methacrylic acid-co-ethyl acrylate), [acetic acid ethenyl ester, polymer with 1-ethenylhexahydro-2H-azepin-2-one and .alpha.-hydro-.omega.-hydroxypoly(oxy-I,2-ethanediyl), graft], or a combination thereof.

12 Claims, 32 Drawing Sheets

(56) References Cited

U.S. PATENT DOCUMENTS

| | | | |
|---|---|---|---|
| 9,254,268 B2 | 2/2016 | Temtsin Krayz et al. | |
| 9,351,957 B2 | 5/2016 | Khera et al. | |
| 9,358,478 B2 | 6/2016 | Dobry et al. | |
| 9,359,426 B2 | 6/2016 | Pearce et al. | |
| 9,408,915 B2 | 8/2016 | Wu et al. | |
| 9,505,725 B2 | 11/2016 | Chakravarty et al. | |
| 9,801,855 B2 | 10/2017 | Bansal et al. | |
| 9,808,426 B2 | 11/2017 | Betageri et al. | |
| 10,058,508 B2 | 8/2018 | Schwarz et al. | |
| 10,071,092 B2 | 9/2018 | Jayaraman et al. | |
| 10,117,937 B2 | 11/2018 | Yao et al. | |
| 10,137,201 B2 | 11/2018 | Brown et al. | |
| 10,189,957 B2 | 1/2019 | Brzeczko et al. | |
| 10,383,941 B2 | 8/2019 | Beyerinck et al. | |
| 10,493,161 B2 | 12/2019 | Warashina et al. | |
| 10,532,028 B2 | 1/2020 | Doney | |
| 10,561,733 B2 | 2/2020 | Weigandt et al. | |
| 10,675,602 B2 | 6/2020 | Friesen et al. | |
| 10,786,486 B2 | 9/2020 | Voudouris | |
| 10,918,603 B2 | 2/2021 | Santos et al. | |
| 11,707,455 B2 | 7/2023 | Dong et al. | |
| 2004/0247624 A1 | 12/2004 | Unger et al. | |
| 2005/0031692 A1* | 2/2005 | Beyerinck | A61K 31/401 424/486 |
| 2005/0048127 A1 | 3/2005 | Brown et al. | |
| 2006/0153913 A1 | 7/2006 | Yamane et al. | |
| 2007/0026072 A1 | 2/2007 | Olsen et al. | |
| 2007/0026073 A1 | 2/2007 | Doney | |
| 2007/0122440 A1 | 5/2007 | Macosko et al. | |
| 2007/0218012 A1 | 9/2007 | Bittorf et al. | |
| 2008/0152717 A1 | 6/2008 | Doney | |
| 2008/0153866 A1 | 6/2008 | Woo et al. | |
| 2008/0181961 A1 | 7/2008 | Brzeczko et al. | |
| 2008/0249317 A1 | 10/2008 | Wang et al. | |
| 2009/0247468 A1 | 10/2009 | Bittorf et al. | |
| 2010/0151037 A1 | 6/2010 | Jiang et al. | |
| 2010/0256074 A1 | 10/2010 | Eidelman et al. | |
| 2010/0272815 A1 | 10/2010 | Khunt et al. | |
| 2011/0142883 A1 | 6/2011 | Dixit et al. | |
| 2011/0217340 A1 | 9/2011 | Angus et al. | |
| 2012/0264833 A1 | 10/2012 | Babcock et al. | |
| 2012/0288542 A1* | 11/2012 | Curatolo | A61K 9/1652 514/57 |
| 2013/0280330 A9 | 10/2013 | Hu et al. | |
| 2014/0212487 A1 | 7/2014 | Mogalian et al. | |
| 2014/0343073 A1 | 11/2014 | Dwivendi et al. | |
| 2015/0018386 A1 | 1/2015 | Dwivedi et al. | |
| 2015/0307540 A1 | 10/2015 | Dwivedi et al. | |
| 2016/0045470 A1 | 2/2016 | Reddy et al. | |
| 2016/0194352 A1 | 7/2016 | Saladi et al. | |
| 2017/0014383 A1 | 1/2017 | Wu | |
| 2017/0037234 A1 | 2/2017 | Prud'Homme et al. | |
| 2017/0281599 A1 | 10/2017 | Desai et al. | |
| 2018/0055845 A1 | 3/2018 | Reents et al. | |
| 2018/0104239 A1 | 4/2018 | Deboeck et al. | |
| 2018/0344646 A1 | 12/2018 | Konagurthu et al. | |
| 2019/0076360 A1 | 3/2019 | Neves et al. | |
| 2019/0083629 A1 | 3/2019 | Vergauwen et al. | |
| 2019/0142756 A1 | 5/2019 | Miller et al. | |
| 2019/0160005 A1 | 5/2019 | Pullagurla et al. | |
| 2019/0231755 A1 | 8/2019 | Kawamura | |
| 2019/0269662 A1 | 9/2019 | Rannard et al. | |
| 2019/0328713 A1 | 10/2019 | Chen et al. | |
| 2019/0365738 A1 | 12/2019 | Desai et al. | |
| 2020/0261449 A1 | 8/2020 | Jain et al. | |
| 2021/0077405 A1 | 3/2021 | Vicente et al. | |
| 2021/0315831 A1 | 10/2021 | Martin et al. | |
| 2021/0347978 A1 | 11/2021 | Durig et al. | |
| 2022/0144835 A1 | 5/2022 | Garmise et al. | |
| 2022/0183981 A1 | 6/2022 | Corson et al. | |
| 2022/0287976 A1 | 9/2022 | Miller et al. | |

FOREIGN PATENT DOCUMENTS

| | | | | |
|---|---|---|---|---|
| EP | 2 832 723 A1 | 2/2015 | |
| EP | 3023110 A1 * | 5/2016 | A61K 31/496 |
| JP | 2004-534811 A | 11/2004 | |
| JP | 2017-048135 A | 3/2017 | |
| WO | WO 2003/000226 | 1/2003 | |
| WO | WO 2005/044824 A2 | 5/2005 | |
| WO | WO 2006/090150 A1 | 8/2006 | |
| WO | WO 2007/016435 A2 | 2/2007 | |
| WO | WO 2007/060384 A2 | 5/2007 | |
| WO | WO 2007/109605 A2 | 9/2007 | |
| WO | WO 2009/084036 A2 | 7/2009 | |
| WO | WO 2011/082426 A1 | 7/2011 | |
| WO | WO 2012/174082 A1 | 12/2012 | |
| WO | WO 2013/040187 A1 | 3/2013 | |
| WO | WO 2013/105894 A1 | 7/2013 | |
| WO | WO 2014/081581 A2 | 5/2014 | |
| WO | WO 2015/138837 A1 | 9/2015 | |
| WO | WO 2016/082705 A1 | 6/2016 | |
| WO | WO 2017/096309 | 6/2017 | |
| WO | WO 2017/108605 A1 | 6/2017 | |
| WO | WO 2018/073839 A1 | 4/2018 | |
| WO | WO 2019/016828 A1 | 1/2019 | |
| WO | WO 2019/019091 A1 | 1/2019 | |
| WO | WO 2019/179598 A1 | 9/2019 | |
| WO | WO 2019/220282 A1 | 11/2019 | |
| WO | WO 2020/099937 A2 | 5/2020 | |
| WO | WO 2020/122243 A1 | 6/2020 | |
| WO | WO 2020/172120 A1 | 8/2020 | |
| WO | WO 2020/210626 A1 | 10/2020 | |
| WO | WO 2020/210629 A1 | 10/2020 | |
| WO | WO 2020/242999 A1 | 12/2020 | |
| WO | WO 2021/150981 | 7/2021 | |

OTHER PUBLICATIONS

Berkenfeld et al., "Inhalable Formulations of Rifampicin by Spray Drying of Supersaturated Aqueous Solutions," *European Journal of Pharmaceutics and Biopharmaceutics*, published online May 22, 2020, 153:14-22.

International Search Report and Written Opinion for PCT/EP2021/070577, Oct. 21, 2021, 21 pages.

International Search Report and Written Opinion for PCT/EP2021/076996, Nov. 3, 2021, 11 pages.

International Search Report and Written Opinion for PCT/EP2022/065249, Apr. 10, 2022, 10 pages.

International Search Report and Written Opinion for PCT/EP2022/065542, Aug. 30, 2022, 13 pages.

International Search Report and Written Opinion for PCT/EP2022/065703, Sep. 27, 2022, 9 pages.

Paudel et al., "Manufacturing of Solid Dispersions of Poorly Water Soluble Drugs by Spray Drying: Formulation and Process Considerations," *International Journal of Pharmaceutics*, published online Jul. 20, 2012, 453(1):253-284.

Saturn Spraying Systems, "Controlling the Temperature of the Spraying Process," published online Jul. 20, 2012, 3 pages.

Friesen et al., "Hydroxypropyl Methylcellulose Acetate Succinate-Based Spray-Dried Dispersions: An Overview," *Molecular Pharmaceutics*, 5(6):1003-1019 (Dec. 1, 2008).

Office Action issued for Japanese Patent Application No. 2023-504521, dated Aug. 1, 2025, 9 pages, with English Translation.

Bristol Myers Squibb, "SPRYCEL® (Dasatinib) Shows Potential as Treatment for Prostate Cancer," https://news.bms.com/news/details/2009/SPRYCEL-Dasatinib-Shows-Potential-as-Treatment-for-Prostate-Cancer/default.aspx, 3 pages (May 12, 2009).

Schade et al., "Dasatinib, a small-molecule protein tyrosine kinase inhibitor, inhibits T-cell activation and proliferation," *Blood*, vol. 111, No. 3, pp. 1366-1377, Feb. 1, 2008.

DrugBank Online, Telaprevir: Uses, Interactions, Mechanism of Action, https://go.drugbank.com/drugs/DB05521, 20 pages (Downloaded Oct. 24, 2025).

Office Action, dated Aug. 8, 2024, issued in corresponding European Patent Application No. 21806613.2, 6 pages.

(56) References Cited

OTHER PUBLICATIONS

Liu et al., "Preparation of Hypromellose Hollow Capsules," *Chin Pharm J.*, Jan. 2018, 53(1), with English-language translation, 20 pages.

Sun et al., "Optimization of Enteric Coating Technology for Hydroxypropyl Methylcellulose Hollow Capsules," *Chinese Journal of Pharmaceuticals*, 2018, 49(7), 975-983, English translation (updated), 9 pages.

Wang, Tianjin University—Master's Degree Thesis, "Novel Process for the Synthesis of Hydroxypropyl Methylcellulose Phthalate (HPMCP), and Preparation of Aqueous Dispersions Thereof," Jun. 1, 2008, with English-language translation, 117 pages.

Examination Report issued for European Patent Application No. 21749144.8, dated Oct. 30, 2025, 8 pages.

Sun et al., "Optimization of Enteric Coating Technology for Hydroxypropyl Methylcellulose Empty Capsules," Chinese Journal of Pharmaceuticals 2018, 49(7), 975-980, with English Translation, 13 pages.

Office Action issued in Japanese Patent Application No. 2023-575797, dated Apr. 7, 2026, 8 pages.

* cited by examiner

MIXED SOLVENTS FOR SPRAY DRYING FOR PREPARATION OF AMORPHOUS SOLID DISPERSIONS

CROSS REFERENCE TO RELATED APPLICATIONS

This is the U.S. National Stage of International Application No. PCT/EP2022/065542, filed Jun. 8, 2022, which was published in English under PCT Article 21(2), which in turn claims the benefit of European Application No. 21179384.9, filed Jun. 15, 2021, U.S. Provisional Application No. 63/209,468, filed Jun. 11, 2021, and U.S. Provisional Application No. 63/208,643, filed Jun. 9, 2021, each of which is incorporated herein in its entirety.

FIELD

The invention discloses a method for preparation of spray dried amorphous solid dispersions comprising an active agent such as an active pharmaceutical ingredient, API, and a dispersion polymer wherein the spray drying is done with a solution of the active agent and of the dispersion polymer in a solvent comprising a mixture of a $C_{1-2}$ alkanol with a $C_{1-2}$ carboxylic acid $C_{1-2}$ alkyl ester, and optionally water.

BACKGROUND OF THE INVENTION

Spray dried amorphous solid dispersions comprising an active pharmaceutical ingredient, API, and a dispersion polymer are typically produced by dissolving the dispersion polymer and the API in a volatile solvent, such as methanol or acetone followed by spray drying. In cases where the API has limited solubility, approximately <4 wt % at room temperature, in the spray drying solvent, an API suspension can be heated to a temperature either below or above the solvent's ambient pressure boiling point, this is known as "hot spray drying process", resulting in a higher dissolved concentration of API. In some cases, even the higher temperatures do not give adequate API concentrations that are economical for a spray drying process, or cause other problems such as chemical degradation of the API, or bear the risk of incomplete API dissolution in the heat exchanger. Alternate, non-preferred volatile solvents can provide increased solubility of the API, but these solvents have other disadvantages that make them less desirable, e.g. high cost, toxicity, poor equipment compatibility, poor commercial availability, high disposal costs, challenges removing to sufficiently low levels, higher viscosity.

WO 2019/220282 A1 discloses in Example 1 spray drying of a solution of erlotinib and a dispersion polymer (PMMAMA or hydroxypropyl methylcellulose acetate succinate H grade) in methanol to provide a spray dried dispersion.

There was a need for a method for preparing spray dried solid dispersion of an active agent and dispersion polymers, which allows for dissolving the APIs in easily processable spray drying solvents at modest temperature, i.e. a temperature below the ambient pressure boiling point, at sufficiently high concentrations to enable economical throughput of spray dried amorphous solid dispersions. The amorphous solid dispersion should be stable over a longer period of time.

It was found that a mixture of a $C_{1-2}$ alkanol with a $C_{1-2}$ carboxylic acid $C_{1-2}$ alkyl ester shows synergistic, also called non-linear, dissolution behaviour, i.e. a mixture provides for higher solubility compared to the, by linear extrapolation from the solubilities of the pure solvents, expected solubilities at the respective weight average of the individual solvents, and may be used as a mixed solvent in such spray drying method. This synergistic behaviour was not expected. Furthermore both a $C_{1-2}$ alkanol and a $C_{1-2}$ carboxylic acid $C_{1-2}$ alkyl ester individually are regarded as poor solvents compared to solvents such as dichloromethane (DCM), tetrahydrofuran (THF) and N-methyl-2-pyrrolidone (NMP), but both are regarded as solvents well suited for spray drying, so a synergistic increase of the solubilities allows for higher concentration of active agent in the spray solution when using these two solvents as a mixture. Increased active agent solubility gives higher manufacturing throughput, and potentially better spray dried particle characteristics than what is achievable with lower solids content spray solutions.

Another advantage is that the two solvents can be mixed with water to provide a ternary mixture and this aqueous ternary mixture of the two solvents with water still provides for the synergistic increase of solubility, thereby also dispersion polymers, such as HPMC, which typically require the presence of some water in order to dissolve in an organic solvent, many be used. The synergistic behaviour of the ternary mixture was also unexpected since water alone is usual regarded being a still poorer solvent than any of the $C_{1-2}$ alcohols and $C_{1-2}$ carboxylic acid $C_{1-2}$ alkyl esters.

Abbreviations and Definitions Used in this Specification

- Active agent As used herein, the term "active agent" refers to a component that exerts a desired physiological effect on a mammal, including but not limited to humans. Synonymous terms include "active ingredient," "active substance," "active component," "active pharmaceutical ingredient," and "drug."
- Amorphous Substantially non-crystalline. Amorphous solids lack a definite crystalline structure and a sharp, well-defined melting point; instead, an amorphous solid melts gradually over a range of temperatures.
- API active pharmaceutical ingredient
- ASD amorphous solid dispersions
- Dispersion A system in which particles are distributed in a continuous phase of a different composition. A solid dispersion is a system in which at least one solid component is distributed in another solid component.
- eq equivalents
- HPMCAS Hydroxypropyl Methylcellulose Acetate Succinate, Hypromellose Acetate Succinate, CAS 71138-97-1
- PVPVA Vinylpyrrolidone-vinyl acetate copolymer
- PXRD powder X-Ray Diffraction
- RH relative humidity
- RT room temperature, for the purpose of the invention RT means temperatures from 20 to 25° C.
- solubility Solubilities stated herein in wt % mean weight of dissolved substance per weight of solvent;
  - solubilities stated herein in mg/ml or in mg/g mean mg of dissolved substance per ml or per mg of solvent;
  - any solubilities herein are determined at room temperature as defined herein, a typical value is 25° C.;
  - if not stated explicitly otherwise.
- Solubilize To make soluble or increase the solubility of.
- Solution A homogeneous mixture composed of two or more substances. A solute (minor component) is dissolved in a solvent (major component). In contrast to a suspension, light passes through a solution without scattering from solute particles.

spray solution As used herein, the term "spray solution" refers to a fluid formed by dissolving an active agent and a dispersion polymer in a solvent and an amount of ammonia. In the case of the active agent, the term "dissolved" has the conventional meaning, indicating that the active agent has gone into solution when combined with the solvent and the amount of ammonia. In the case of dispersion polymers, the term "dissolved" can take a broader definition. For some dispersion polymers, the term dissolved can mean that the dispersion polymer has gone into solution and has dissolved in the conventional sense, or it can mean that the dispersion polymer is dispersed or highly swollen with the solvent such that it acts as if it were in solution, or it can mean that a portion of the dispersion polymer molecules are in solution and the remaining dispersion polymer molecules are dispersed or highly swollen with solvent. Any suitable technique may be used to determine if the active agent and dispersion polymer are dissolved. Examples include dynamic or static light scattering analysis, turbidity analysis, and visual observations.

wt % weight %

SUMMARY OF THE INVENTION

Subject of the invention is a method for preparing an amorphous solid dispersion by spray drying a spray solution comprising a) a mixed solvent, the mixed solvent comprising
  i. a solvent 1 selected from the group consisting of methyl acetate, methyl formate, ethyl acetate, ethyl formate and mixtures thereof;
  ii. a solvent 2 selected from the group consisting of methanol, ethanol and mixtures thereof;
  with the ratio (w:w) of solvent 1 to solvent 2 being from 10:90 to 90:10;
b) an active agent;
c) a dispersion polymer.

DETAILED DESCRIPTION OF THE INVENTION

Figure 1:
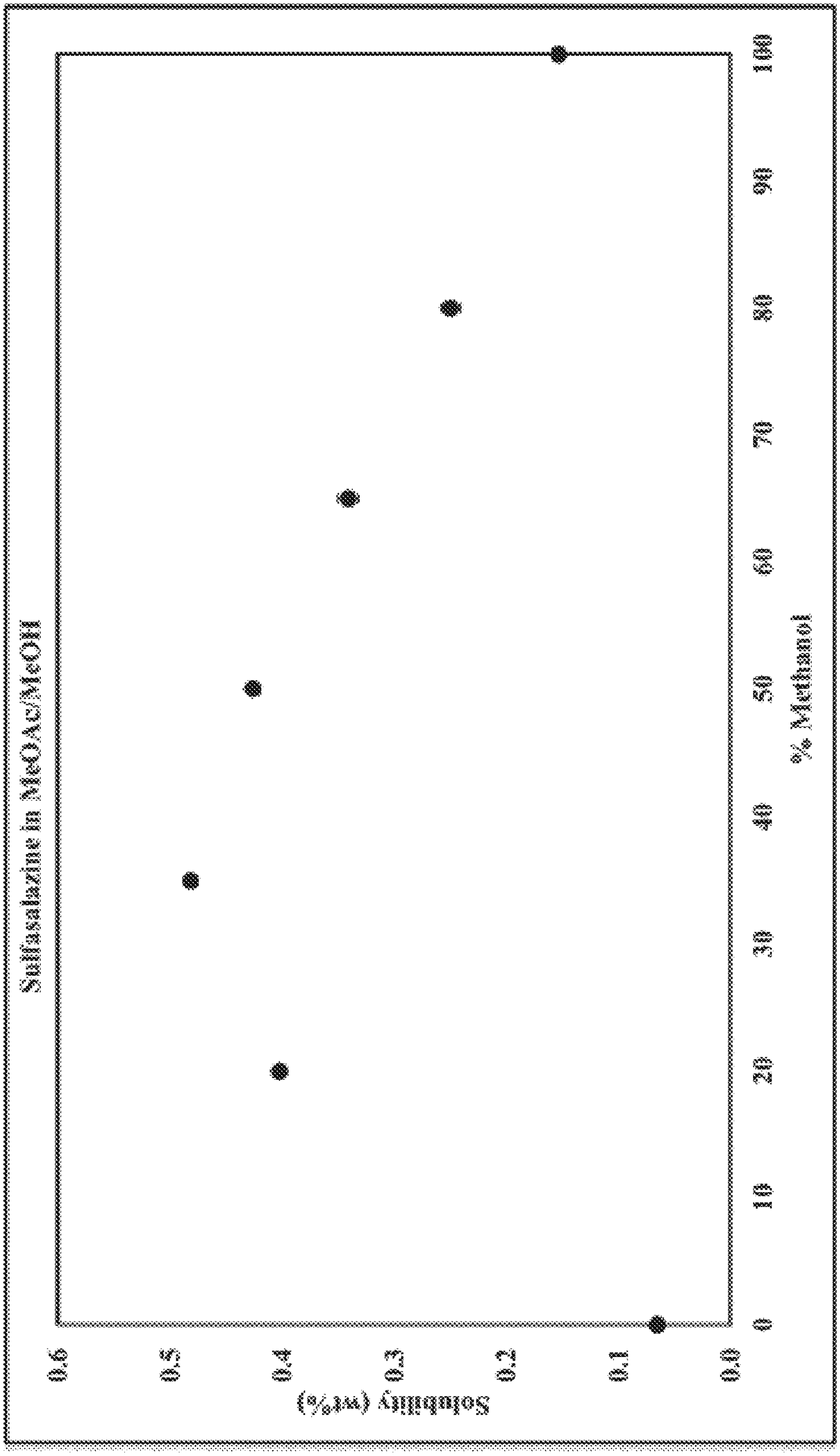
FIG. 1: graphically presentation of the data of table 1: Solubility in wt %, the saturation concentration of Sulfasalazine in MeOAc/MeOH.

The solution of the active agent in the spray solution is a stable solution.

The spray solution has not more than one liquid phase.

The liquid in the spray solution may comprise in addition to the mixed solvent further solvents.

The amount of mixed solvent in the liquid of the spray solution may be at least 50 wt %, preferably at least at least 60 wt %, more preferably at least 70 wt %, even more preferably at 80 wt %, especially at least 90 wt %, more especially at least 95 wt %; with the wt % being based on the weight of the liquid of the spray solution;

in one embodiment the liquid in the spray solution consists of the mixed solvent.

The active agent is a biologically active compound. The biologically active compound may be desired to be administered to a patient in need of active agent.

A biologically active compound may be a drug, medicament, pharmaceutical, therapeutic agent, nutraceutical, agrochemical, fertilizer, pesticide, herbicide, nutrient, or an active pharmaceutical ingredient, API; preferably an API.

The active agent may be one or more active agents; the spray dried amorphous solid dispersion may contain one or more active agents.

Preferably, the active agent has a low solubility in solvent 1 and in solvent 2, such as in methanol or in methyl acetate, especially in methanol, e.g. a low solubility of less than 3 wt %, or even less than 2 wt %, or even less than 1 wt %, or even less than 0.5 wt %, or even less than 0.25 wt %.

Preferably the solubility of said active agent in the mixed solvent is at least 1.1 fold, more preferably at least 1.25 fold, even more preferably at least 1.5 fold, even more preferably at least 1.75 fold, even more preferably at least 2 fold, especially at least 3 fold, more especially at least 4 fold, higher than the solubility of said active agent in either solvent 1 or solvent 2 alone.

Preferably the solubility of said active agent in the spray solution is at least 1.1 fold, more preferably at least 1.25 fold, even more preferably at least 1.5 fold, even more preferably at least 1.75 fold, even more preferably at least 2 fold, especially at least 3 fold, more especially at least 4 fold, higher than the solubility of said active agent in either solvent 1 or solvent 2 alone.

Preferably the concentration of said active agent dissolved in the mixed solvent is at least 1.1 fold, more preferably at least 1.25 fold, even more preferably at least 1.5 fold, even more preferably at least 1.75 fold, even more preferably at least 2 fold, especially at least 3 fold, more especially at least 4 fold, higher than the solubility of said active agent in either solvent 1 or solvent 2 alone.

Preferably the concentration of said active agent dissolved in the spray solution is at least 1.1 fold, more preferably at least 1.25 fold, even more preferably at least 1.5 fold, even more preferably at least 1.75 fold, even more preferably at least 2 fold, especially at least 3 fold, more especially at least 4 fold, higher than the solubility of said active agent in either solvent 1 or solvent 2 alone.

The active agent and the dispersion polymer are preferably homogeneously mixed in the spray dried amorphous solid dispersion.

In a spray dried amorphous solid dispersion containing the active agent and the dispersion polymer, the active agent may be homogeneously and preferably also molecularly dispersed in the dispersion polymer. The active agent and the dispersion polymer may form a solid solution in the spray dried amorphous solid dispersion.

The active agent may be amorphous or substantially amorphous in the spray dried amorphous solid dispersion; substantially means that at least 80 wt %, preferably at least 90 wt %, more preferably at least 95 wt %, even more preferably at least 98 wt %, especially at least 99% wt %, of the active agent is amorphous; the wt % being based on the total weight of active agent in the spray dried amorphous solid dispersion. The amorphous nature of active agent may be evidenced by a lack of sharp Bragg diffraction peaks in the x-ray pattern when spray dried amorphous solid dispersion is analyzed by a powder X-Ray Diffraction, PXRD. Possible parameters and settings for a x-ray diffractometer are equipment with a Cu-Kalpha source, setting in modified parallel beam geometry between 3 and 40° 2Theta and a scan rate of 2°/min with a 0.0° step size. Another evidence for the amorphous nature of active agent in the spray dried amorphous solid dispersion may be a single glass transition temperature, Tg. A single Tg is also evidence of a homogeneous mixture of amorphous active agent and dispersion polymer. Samples as such without any further sample preparation may be used for the determination of the Tg, the determination may run for example in modulated mode at a scan rate of 2.5° C./min, modulation of ±1.5° C./min, and a scan range from 0 to 180° C. The amorphous nature of the active agent shows a Tg which is equal to the Tg of neat dispersion polymer or which is between the Tg of the dispersion polymer and the Tg of the active agent. The Tg of the spray dried amorphous solid dispersion is often similar to the weighted average of the Tg of the active agent and the Tg of the dispersion polymer.

The amount of active agent in the spray solution may be at least 0.5 wt %, preferably at least 1 wt %, with the wt % being based on the weight of the spray solution.

The amount of active agent in the spray solution may be up to 10 wt %, preferably up to 7.5 wt %, more preferably up to 5 wt %, with the wt % being based on the weight of the spray solution.

Any of the lower limits may be combined with any of the upper limits of active agent in the spray solution.

For example, possible amounts of active agent in the spray solution may be from 0.5 wt % to 10 wt %, preferably from 1 wt % to 10 wt %, more preferably from 1 wt % to 7.5 wt %, with the wt % being based on the weight of the spray solution.

The mixed solvent may comprise the combinations methyl acetate/methanol, methyl acetate/ethanol, ethyl acetate/methanol, ethyl acetate/ethanol, methyl formate/methanol, methyl formate/ethanol, ethyl formate/methanol, and ethyl formate/ethanol;

preferably methyl acetate/methanol, methyl acetate/ethanol, ethyl acetate/ethanol, and ethyl formate/methanol;

more preferably methyl acetate/methanol, methyl acetate/ethanol, and ethyl acetate/ethanol;

even more preferably the mixed solvent comprises the combinations methyl acetate/methanol or ethyl acetate/ethanol;

in one embodiment, the mixed solvent comprises the combination methyl acetate/methanol.

In one embodiment, the mixed solvent is not methanol/ethyl-acetate.

The ratio (w:w) of solvent 1:solvent 2 may be from 10:90 to 90:10, preferably from 20:80 to 80:20, more preferably from 30:70 to 70:30.

The combined amount of solvent 1 and solvent 2 in the mixed solvent may be at least 70 wt %, preferably at least at least 80 wt %;

also a higher combined amount of solvent 1 and solvent 2 in the mixed solvent may be used, such as at least 85 wt %, or preferably at least 90 wt %, or at least 95 wt %; with the wt % being based on the weight of the mixed solvent.

In one embodiment, the mixed solvent consists of a mixture of solvent 1 and solvent 2; preferably, solvent 1 consists of only one of the possible individual solvents 1 and solvent 2 consists of only one of the possible individual solvents 2;

with solvent 1 and solvent 2 and their embodiments and combinations as defined herein.

The mixed solvent may further comprise water.

The amount of water is chosen to be such that the spray solution has not more than one liquid phase.

When the mixed solvent comprises water, then the mixed solvent comprises not more than 30 wt %, preferably not more than 27.5 wt %, more preferably not more than 25 wt %, even more preferably not more than 22.5 wt %, especially not more than 20 wt %;

also lower amount of water may be used, such as not more than 15 wt %, or not more than 10 wt %, or not more than 5 wt %, of water, with the wt % being based on the weight of the mixed solvent.

When the mixed solvent comprises water, then the mixed solvent may comprise at least 0.5 wt %, preferably at least 1 wt %, more preferably at least 2 wt %; even more preferably at least 5 wt %, of water, with the wt % being based on the weight of the mixed solvent.

In one embodiment, the mixed solvent consists of a mixture of solvent 1 and solvent 2 and water;

preferably, solvent 1 consists of only one of the possible individual solvents 1 and solvent 2 consists of only one of the possible individual solvents 2.

In one embodiment, the mixed solvent consists of a mixture of solvent 1 and solvent 2; preferably, solvent 1 consists of only one of the possible individual solvents 1 and solvent 2 consists of only one of the possible individual solvents 2.

In one embodiment, solvent 1 consists of only one of the possible individual solvents 1 and solvent 2 consists of only one of the possible individual solvents 2.

The spray solution may comprise one or more dispersion polymers, preferably 1, 2, 3 or 4, more preferably 1, 2 or 3, even more preferably 1 or 2 dispersion polymers.

The dispersion polymer may be a pharmaceutically acceptable dispersion polymer.

Suitable dispersion polymer include, but are not limited to, hydroxypropyl methylcellulose acetate succinate (HPMCAS), hydroxypropyl methylcellulose phthalate (HPMCP), hydroxypropyl methyl cellulose (HPMC), hydroxypropyl cellulose (HPC), cellulose acetate phthalate (CAP), carboxymethyl ethyl cellulose (CMEC), polyvinylpyrrolidone (PVP), poly(vinylpyrrolidone-co-vinyl acetate) (PVPVA), polymethacrylates such as poly(methacrylic acid-co-methyl methacrylate) (PMMAMA) or poly(methacrylic acid-co-ethyl acrylate), [acetic acid ethenyl ester, polymer with 1-ethenylhexahydro-2H-azepin-2-one and .alpha.-hydro-.omega.-hydroxypoly(oxy-1,2-ethanediyl), graft], or a combination thereof.

Suitable polymethacrylates, such as PMMAMA polymers, include, but are not limited to, poly(methacrylic acid-co-methyl methacrylate) 1:1 (for example Eudragit® L100), and poly(methacrylic acid-co-methyl methacrylate) 1:2 (for example Eudragit® S100). Eudragit® are polymer products of Evonik Industries AG, 45128 Essen, Germany.

The poly(methacrylic acid-co-ethyl acrylate) may be poly (methacrylic acid-co-ethyl acrylate) 1:1.

[Acetic acid ethenyl ester, polymer with 1-ethenylhexahydro-2H-azepin-2-one and .alpha.-hydro-.omega.-hydroxypoly(oxy-1,2-ethanediyl), graft] is a polymethacrylate and is available as Soluplus® from BASF, 67056 Ludwigshafen, GERMANY.

In a preferred embodiment, the dispersion polymer is chosen from HPMCAS, HPMC, PVPVA, PVP, polymethacrylates, HPMCP, CMEC, CAP.

In another preferred embodiment, the dispersion polymer is chosen from HPMCAS, HPMC, PVPVA, PVP, polymethacrylates, HPMCP, CMEC, CAP, [Acetic acid ethenyl ester, and polymer with 1-ethenylhexahydro-2H-azepin-2-one and .alpha.-hydro-.omega.-hydroxypoly(oxy-1,2-ethanediyl), graft].

In another more preferred embodiment, the dispersion polymer is chosen from HPMCAS, PVPVA, polymethacrylates, HPMCP, CMEC, CAP.

In another preferred embodiment, the dispersion polymer is chosen from HPMCAS, PVPVA, polymethacrylates, HPMCP, CMEC, CAP, [Acetic acid ethenyl ester, and polymer with 1-ethenylhexahydro-2H-azepin-2-one and .alpha.-hydro-.omega.-hydroxypoly(oxy-1,2-ethanediyl), graft].

In one embodiment the dispersion polymer is PMMAMA, HPMCAS, HPMC, PVPVA or PVP;

in another embodiment the dispersion polymer is HPMC;

in another embodiment the dispersion polymer is PMMAMA, HPMCAS, PVPVA or PVP;

in another embodiment the dispersion polymer is PMMAMA, HPMCAS or PVPVA;

in another embodiment the dispersion polymer is PVP;

in another embodiment the dispersion polymer is HPMCAS.

Preferred embodiments of HPMCAS are

HPMCAS with an acetyl content from 5 to 9 wt % and a succinoyl content from 14 to 18 wt %, HPMCAS with an acetyl content from 7 to 11 wt % and a succinoyl content from 10 to 14 wt %, or HPMCAS with an acetyl content from 10 to 14 wt % and a succinoyl content from 4 to 8 wt %;

more preferably

HPMCAS with an acetyl content from 5 to 7 wt % and a succinoyl content from 14 to 16 wt %, HPMCAS with an acetyl content from 7 to 9 wt % and a succinoyl content from 10 to 12 wt %, or HPMCAS with an acetyl content from 11 to 13 wt % and a succinoyl content from 5 to 7 wt %;

with the wt % being based on the weight of HPMCAS.

When the dispersion polymer is HPMC, preferably the mixed solvent further comprises water; with the amount of water and all its embodiments as stated herein, for example from 10 to 30 wt %, or from 15 to 30 wt %, or from 20 to 30 wt %, with the wt % being based on the weight of the mixed solvent.

The dispersion polymer and the mixed solvent are chosen such that the dispersion polymer dissolves in the mixed solvent.

The dispersion polymer is preferably present in the spray solution in a dissolved state, the amounts of dispersion polymer and of mixed solvent are chosen respectively.

For example amounts of dispersion polymer in the spray solution may be from 0.5 wt % to 25 wt %, preferably from 1 wt % to 20 wt %, more preferably from 2.5 wt % to 15 wt %, even more preferably from 3 wt % to 10 wt %, with the wt % being based on the weight of the spray solution.

Amounts of dispersion polymer and of active agent in the spray solution are chosen such that a predefined amount of dispersion polymer and of active agent in the spray dried amorphous solid dispersion are provided.

The spray dried amorphous solid dispersion may comprise from 1 to 99 wt %, preferably from 10 to 95 wt %, more preferably from 10 to 80 wt %, even more preferably from 20 to 60 wt %, of active agent, the wt % being based on the weight of the spray dried amorphous solid dispersion.

The spray dried amorphous solid dispersion may comprise from 1 to 99 wt %, preferably from 20 to 90 wt %, more preferably from 40 to 80 wt %, of the dispersion polymer, the wt % being based on the weight of the spray dried amorphous solid dispersion.

Preferably, the combined content of active agent and dispersion polymer in spray dried amorphous solid dispersion is from 65 to 100 wt %, more preferably from 67.5 to 100 wt %, even more preferably from 80 to 100 wt %; especially from 90 to 100 wt %; more especially from 95 to 100 wt %; the wt % being based on the weight of the spray dried amorphous solid dispersion.

In one embodiment, the spray dried amorphous solid dispersion consists of active agent and dispersion polymer.

Relative amounts (w:w) of active agent to dispersion polymer in spray dried amorphous solid dispersion may be from 50:1 to 1:50, preferably from 25:1 to 1:25, more preferably from 10:1 to 1:10, even more preferably from 5:1 to 1:5.

An embodiment of the invention is a method for preparing an amorphous solid dispersion by spray drying a spray solution comprising a) a mixed solvent, the mixed solvent comprising
    i. a solvent 1 selected from the group consisting of methyl acetate, methyl formate, ethyl acetate, ethyl formate and mixtures thereof;
    ii. a solvent 2 selected from the group consisting of methanol, ethanol and mixtures thereof;
    with the ratio (w:w) of solvent 1 to solvent 2 being from 10:90 to 90:10;
b) an active agent;
c) HPMC as a dispersion polymer;

preferably the mixed solvent furthers comprise water; with the amount of water and all its embodiments as stated herein.

An embodiment of the invention is a method for preparing an amorphous solid dispersion by spray drying a spray solution comprising a) a mixed solvent, the mixed solvent comprising
    i. a solvent 1 selected from the group consisting of methyl acetate, methyl formate, ethyl acetate, ethyl formate and mixtures thereof;
    ii. a solvent 2 selected from the group consisting of methanol, ethanol and mixtures thereof;
    with the ratio (w:w) of solvent 1 to solvent 2 being from 10:90 to 90:10;
b) an active agent;
c) PVP as a dispersion polymer;

provided that said mixed solvent does not consist of methanol and ethyl acetate.

An embodiment of the invention is a method for preparing an amorphous solid dispersion by spray drying a spray solution comprising a) a mixed solvent, the mixed solvent comprising
    i. a solvent 1 selected from the group consisting of methyl acetate, methyl formate, ethyl acetate, ethyl formate and mixtures thereof;
    ii. a solvent 2 selected from the group consisting of methanol, ethanol and mixtures thereof;
    with the ratio (w:w) of solvent 1 to solvent 2 being from 10:90 to 90:10;
b) an active agent;
c) a dispersion polymer selected from the group consisting of: hydroxypropyl methylcellulose acetate succinate (HPMCAS), hydroxypropyl methylcellulose phthalate (HPMCP), hydroxypropyl cellulose (HPC), cellulose acetate phthalate (CAP), carboxymethyl ethyl cellulose (CMEC), poly(vinylpyrrolidone-co-vinyl acetate) (PVPVA), polymethacrylates such as poly (methacrylic acid-co-methyl methacrylate) (PMMAMA) or poly(methacrylic acid-co-ethyl acrylate), [acetic acid ethenyl ester, polymer with 1-ethenylhexahydro-2H-azepin-2-one and .alpha.-hydro-.omega.-hydroxypoly(oxy-1,2-ethanediyl), graft], or a combination thereof.

The spray solution may be fed into the spray dryer with a temperature of the spray solution up to the boiling point of the spray solution at ambient pressure; preferably with a temperature of from 4° C. to the boiling point of the spray solution at ambient pressure, preferably from 4° C. to a temperature below the boiling point of the spray solution at ambient pressure. In the context of this invention the term “the spray solution may be fed into the spray dryer with a temperature of the spray solution” means that “the spray solution is spray dried with a temperature of the spray solution”.

The spray drying may be done with an inlet temperature of from 60 to 165° C., preferably from 80 to 140° C.

The spray drying may be done with an outlet temperature equal to or less than the boiling point of the mixed solvent, such as with an outlet temperature from 20° C. to a temperature of 10° C. below the boiling point of the mixed solvent.

The spray drying may be done with any inert gas commonly used for spray drying, such as nitrogen.

The spray solution may further comprise a dissolved surfactant.

The surfactant may be for example a fatty acid and alkyl sulfonate, docusate sodium (for example available from Mallinckrodt Spec. Chem., St. Louis, Mo.), polyoxyethylene sorbitan fatty acid esters (for example Tween®, available from ICI Americas Inc, Wilmington, Del., or Liposorb® P-20, available from Lipochem Inc, Patterson, N.J., or Capmul® POE-0, available from Abitec Corp., Janesville, Wis.), natural surfactants such as sodium taurocholic acid, 1-palmitoyl-2-oleoyl-sn-glycero-3-phosphocholine, lecithin, other phospholipids and mono- and diglycerides, vitamin E TPGS, PEO-PPO-PEO triblock copolymers (for example known under the tradename pluronics), or PEO (PEO are also called PEG, polyethyleneglycols (PEG)).

The amount of surfactant in the spray solution may be such that an amount of surfactant in the spray dried amorphous solid dispersion of up to 10 wt % or up to 5 wt % is provided, the wt % being based on the weight of the spray dried amorphous solid dispersion.

The spray solution may further comprises pharmaceutically acceptable excipients, such as fillers, disintegrating agents, pigments, binders, lubricants, flavorants, and so forth which can be used for customary purposes and in typical amounts known to the person skilled on the art.

The spray dried amorphous solid dispersion may comprise residual mixed solvent, that is residual solvent 1 or residual solvent 2 or both, the total content of residual solvent in the spray dried amorphous solid dispersion may be 5’000 ppm or less, preferably 3’000 ppm or less, more preferably 500 ppm or less, even more preferably of 100 ppm or less, the ppm being based on the weight of the spray dried amorphous solid dispersion.

Any residual content of solvent in the spray dried amorphous solid dispersion may be reduced to a desired predefined and final content of solvent by submitting the spray dried amorphous solid dispersion after the spray drying to a second drying. Secondary drying may be done using a tray dryer or any agitated dryer known to the skilled person for drying solids.

Further subject of the invention is a spray dried amorphous solid dispersion, wherein the spray dried amorphous solid dispersion is obtainable by the method for preparing an amorphous solid dispersion by spray drying a spray solution;

with the method and the amorphous solid dispersion and the spray solution as defined herein, also with all their embodiments.

EXAMPLES

Materials and Abbreviations gefitinib crystalline gefitinib, free base, CAS 184475-35-2, compound of formula (1), LC Laboratories, Woburn, MA 01801, US (1)

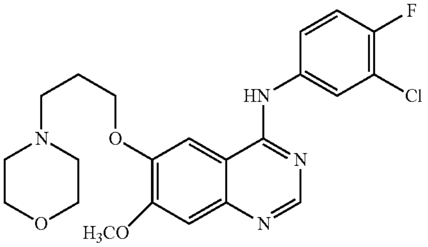

nilotinib crystalline nilotinib, CAS 641571-10-0, compound of formula (2), LC Laboratories, Woburn, MA 01801, US (2)

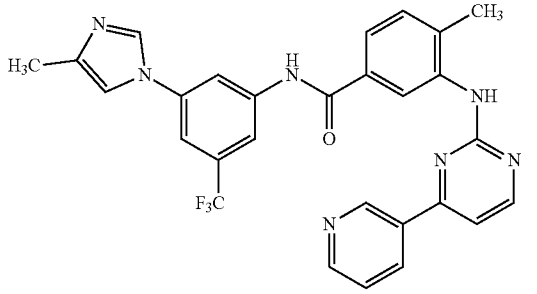

sulfasalazine crystalline sulfasalazine, CAS 599-79-1, compound of formula (3), TCI Chemical Co., Portland, OR 97203, US (3)

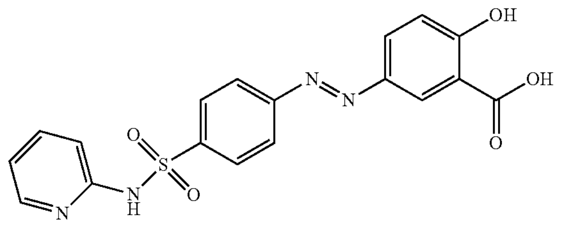

Eudragit L100 a PMMAMA polymer, Evonik Industries AG, 45128 Essen, Germany

HPMCAS-MG hydroxypropyl methylcellulose acetate succinate, Shin-Etsu Polymer Co., Ltd., Tokyo 101-0041 Japan, such as AQOAT® MG (also called AS-MG).

The letter M specifies the grade and distinguish the contents of acetyl and succinoyl groups. Other grades are designated with the letters L (HPMCAS-L) and H (HPMCAS-H). The Letter G represents granular grade with a Mean Particle Size of 1 mm, a letter F instead of a G would represent micronized grade with a Mean Particle Size of 5 micrometer. Various contents and parameters of these grades are given in Table 15.

TABLE 15

| Grade | Viscosity (mPa * s) (a) | Methoxy content [wt %](c) | Hydroxy-propoxy content [wt %](c) | Acetyl content [wt %] range/ preferred(c) | Succinoyl content [wt %] range/ preferred(c) | Tg [° C.] (b) |
|---|---|---|---|---|---|---|
| L | 2.4 to 3.6 | 20 to 24 | 5 to 9 | 5 to 9/6 | 14 to 18/15 | 122 |
| M | 2.4 to 3.6 | 21 to 25 | 5 to 9 | 7 to 11/8 | 10 to 14/11 | 122 |
| H | 2.4 to 3.6 | 22 to 26 | 6 to 10 | 10 to 14/12 | 4 to 8/6 | 122 |

(a) Viscosity of 2 w/w % solution of sodium hydroxide aqueous solution at 20° C.

(b) Tg of the HPMCAS was determined by DSC experiment under the following test condition:

Equipment: DSC Q2000 (TA Instruments. Japan)

Heating rate: 10° C./min

Referred to the second heating run $N_2$ gas atmosphere

Sample size 3 mg (c)the wt % based on the weight of the HPMCAS

HPMC E3 hydroxypropyl methylcellulose, trade name METHOCEL E3 Premium LV, DuPont de Nemours, Inc., Wilmington, Delaware, US PVPVA64 vinylpyrrolidone-vinyl acetate, trade name Kollidon VA64, BASF, Ludwigshafen, Germany Method Determination of Saturation Concentration of Drug in Solvent Mixed solvents were prepared by premixing individual solvents by weight. Solvent ratios are the weight percent of each component.

Saturated solutions were made by adding excess crystalline API to 2 mL individual solvent or mixed solvent and stirring for 24 h at 25° C. Each sample was then filtered through a 1 micrometer glass filter. An aliquot of 50 microliter was run on the TA Inc. Discovery TGA, TA Instruments, New Castle, DE 19720, US, isothermally at 90° C. for 10 min to remove solvent and measure the mass of the API in solution.

Results are given in the tables. The mg/ml values are the measured values, the wt % values are calculated from density estimates of the mixed solvent.

Example 1: Solubilities in MeOAc:MeOH

Example 1a: Sulfasalazine

Table 1 shows the saturation concentration of Sulfasalazine in MeOAc/MeOH.

FIG. 1 shows a graphically presentation of the data of table 1: Solubility in wt %.

Figure 2:
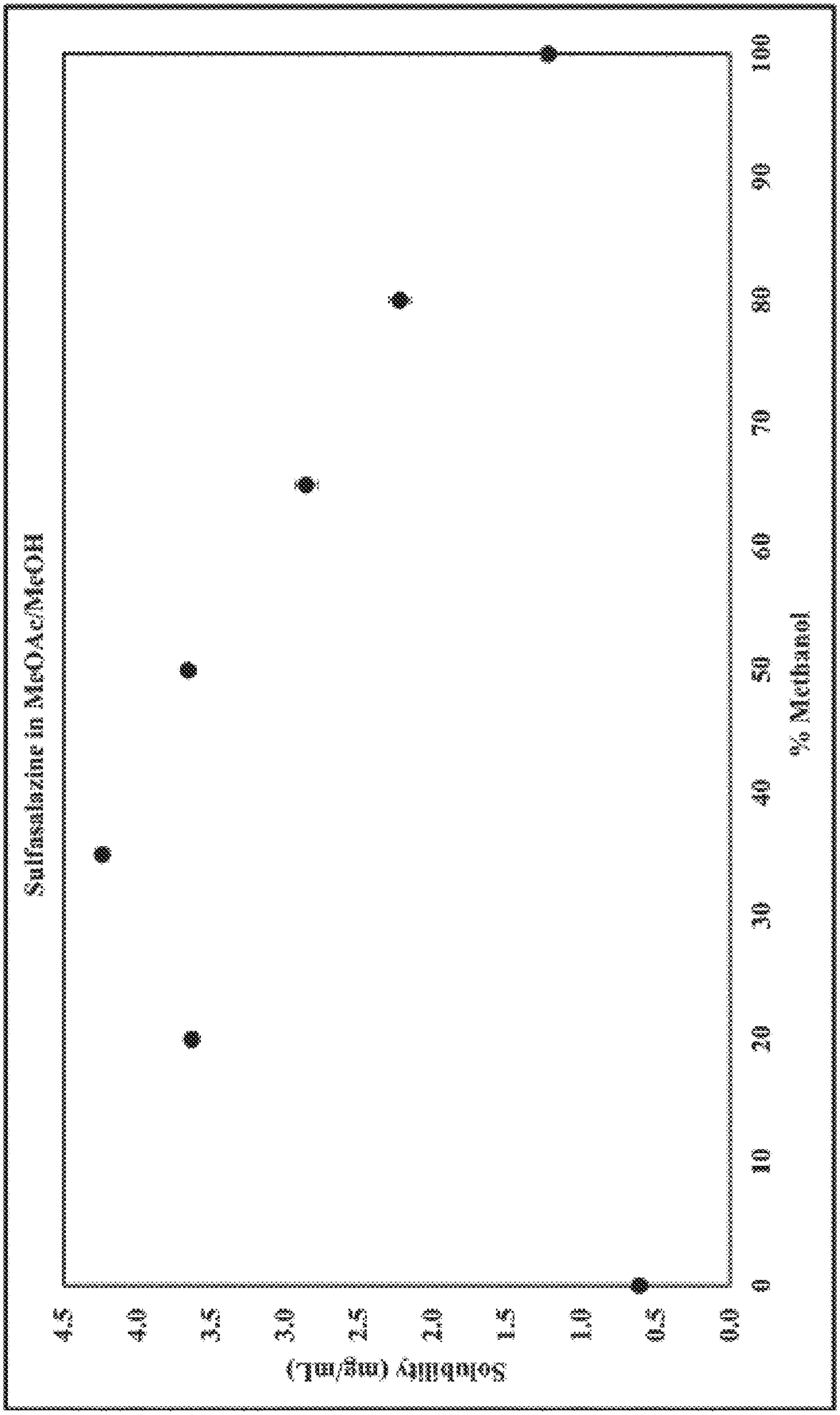
FIG. 2: graphically presentation of the data of table 1: Solubility in mg/ml, the saturation concentration of Sulfasalazine in MeOAc/MeOH.

FIG. 2 shows a graphically presentation of the data of table 1: Solubility in mg/ml.

TABLE 1

| Sulfasalazine | | | | | | | |
|---|---|---|---|---|---|---|---|
| | Solvent Ratio MeOAc:MeOH | | | | | | |
| | 100:0 | 80:20 | 65:35 | 50:50 | 35:65 | 20:80 | 0:100 |
| Concentration (wt %) | 0.065 ± 0.003 | 0.403 ± 0.003 | 0.482 ± 0.003 | 0.426 ± 0.001 | 0.341 ± 0.009 | 0.250 ± 0.009 | 0.153 ± 0.004 |
| Concentration (mg/mL) | 0.61 ± 0.03 | 3.63 ± 0.03 | 4.23 ± 0.02 | 3.65 ± 0.01 | 2.85 ± 0.08 | 2.22 ± 0.07 | 1.21 ± 0.03 |

Example 1b: Nilotinib

Table 3 shows the saturation concentration of Nilotinib in MeOAc/MeOH.

Figure 5:
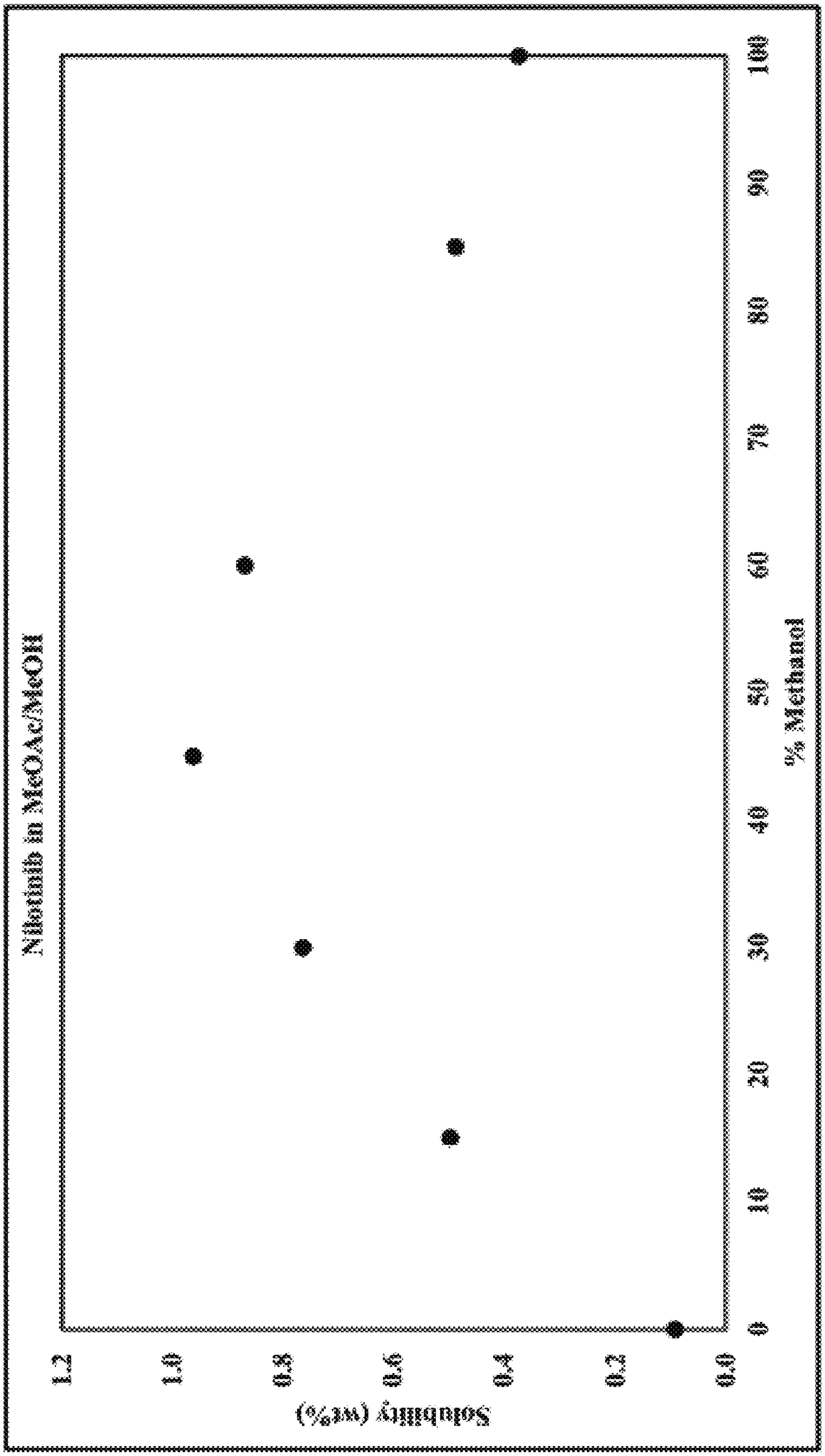
FIG. 5: graphically presentation of the data of table 3: Solubility in wt %, the saturation concentration of Nilotinib in MeOAc/MeOH.

FIG. 5 shows a graphically presentation of the data of table 3: Solubility in wt %.

Figure 6:
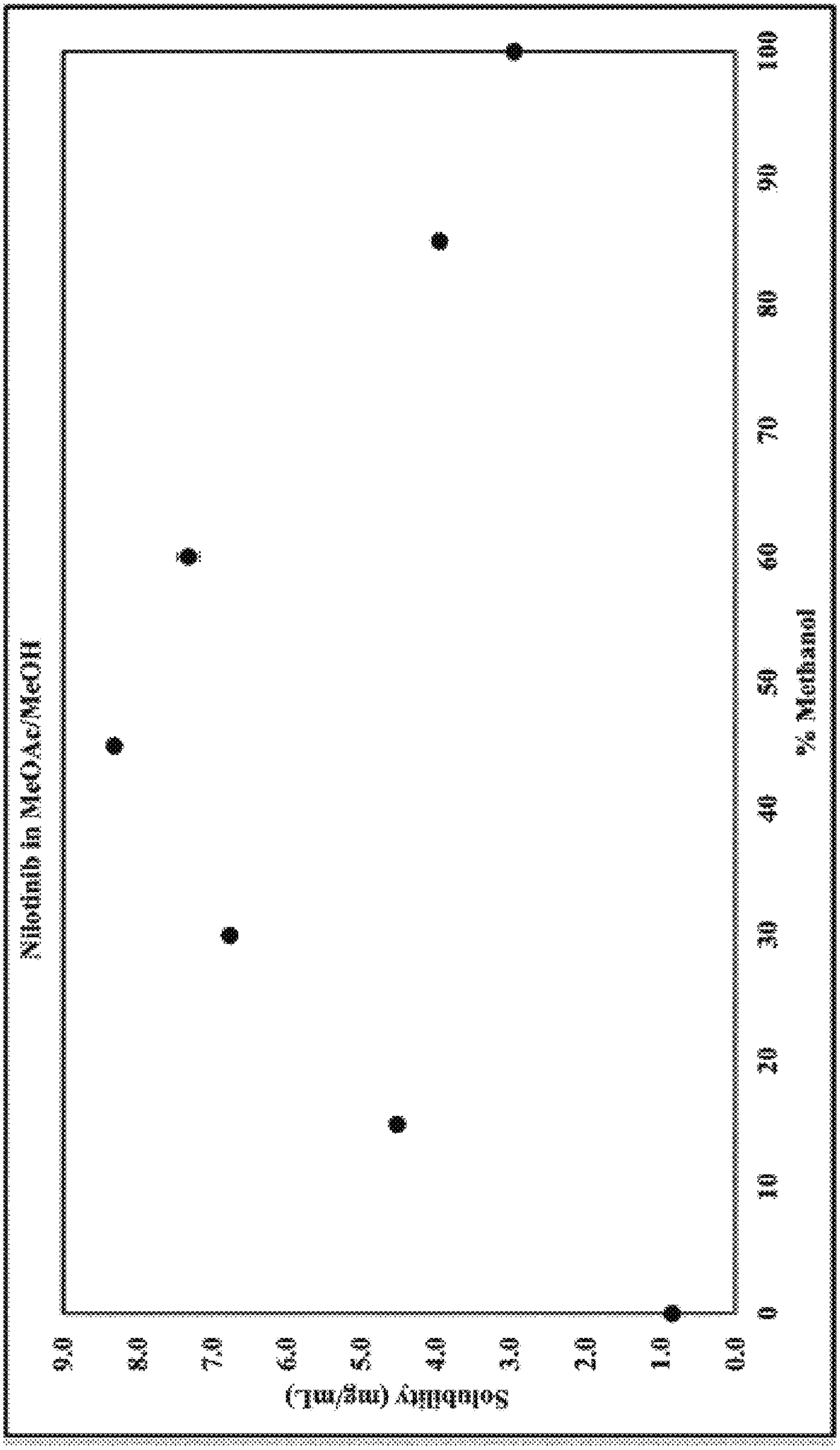
FIG. 6: graphically presentation of the data of table 3: Solubility in mg/ml, the saturation concentration of Nilotinib in MeOAc/MeOH.

FIG. 6 shows a graphically presentation of the data of table 3: Solubility in mg/ml.

TABLE 3

| Nilotinib | | | | | | | |
|---|---|---|---|---|---|---|---|
| | Solvent Ratio (MeOAc:MeOH) | | | | | | |
| | 100:0 | 85:15 | 70:30 | 55:45 | 40:60 | 15:85 | 0:100 |
| Concentration (wt %) | 0.091 ± 0.003 | 0.496 ± 0.001 | 0.763 ± 0.009 | 0.961 ± 0.001 | 0.868 ± 0.007 | 0.486 ± 0.002 | 0.371 ± 0.002 |
| Concentration (mg/mL) | 0.85 ± 0.03 | 4.51 ± 0.01 | 6.76 ± 0.08 | 8.31 ± 0.01 | 7.32 ± 0.06 | 3.94 ± 0.02 | 2.94 ± 0.02 |

Example 1c: Gefitinib

Table 5 shows the saturation concentration of Gefitinib in MeOAc/MeOH.

Figure 9:
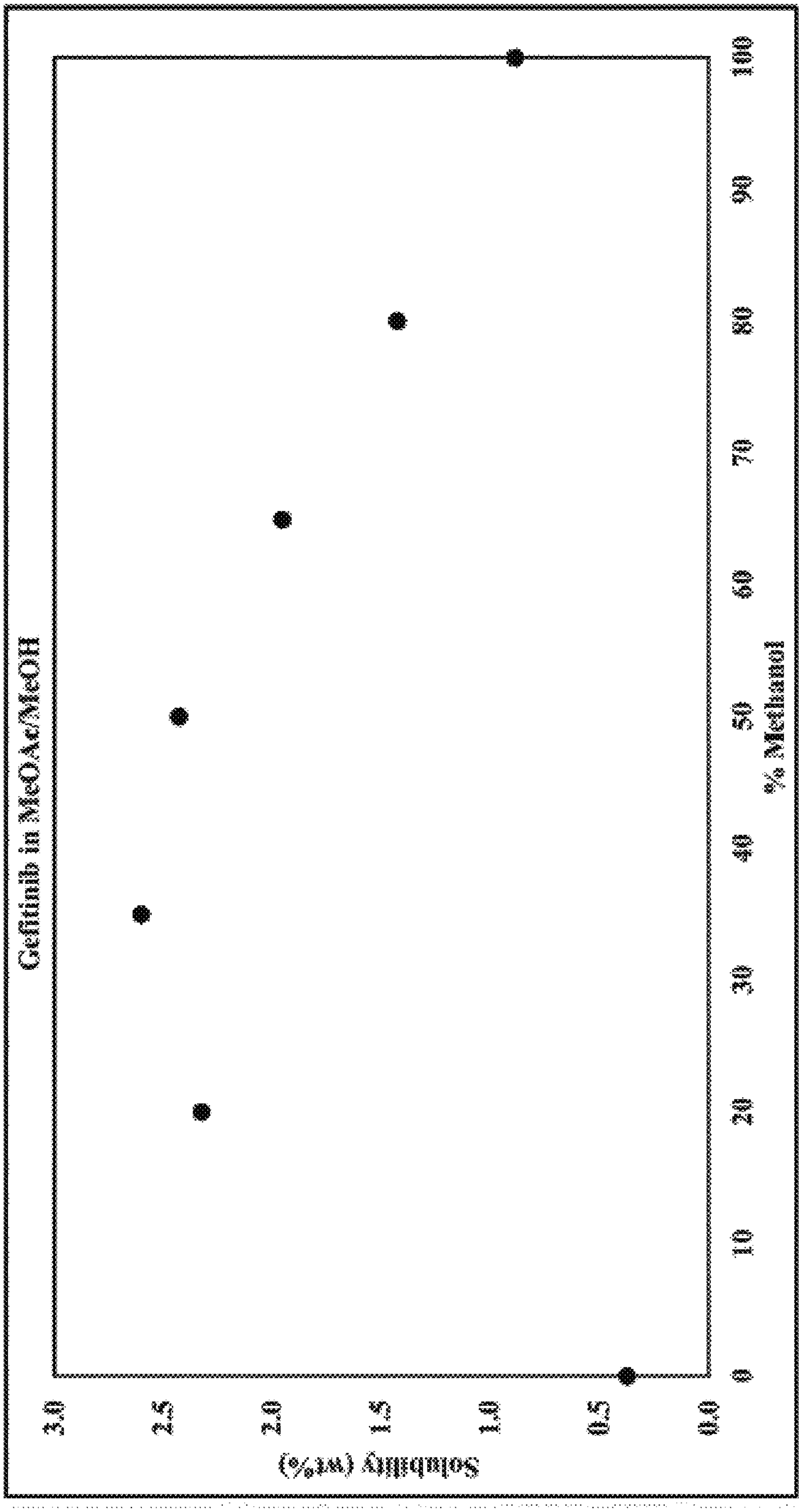
FIG. 9: graphically presentation of the data of table 5: Solubility in wt %, the saturation concentration of Gefitinib in MeOAc/MeOH.

FIG. 9 shows a graphically presentation of the data of table 5: Solubility in wt %.

Figure 10:
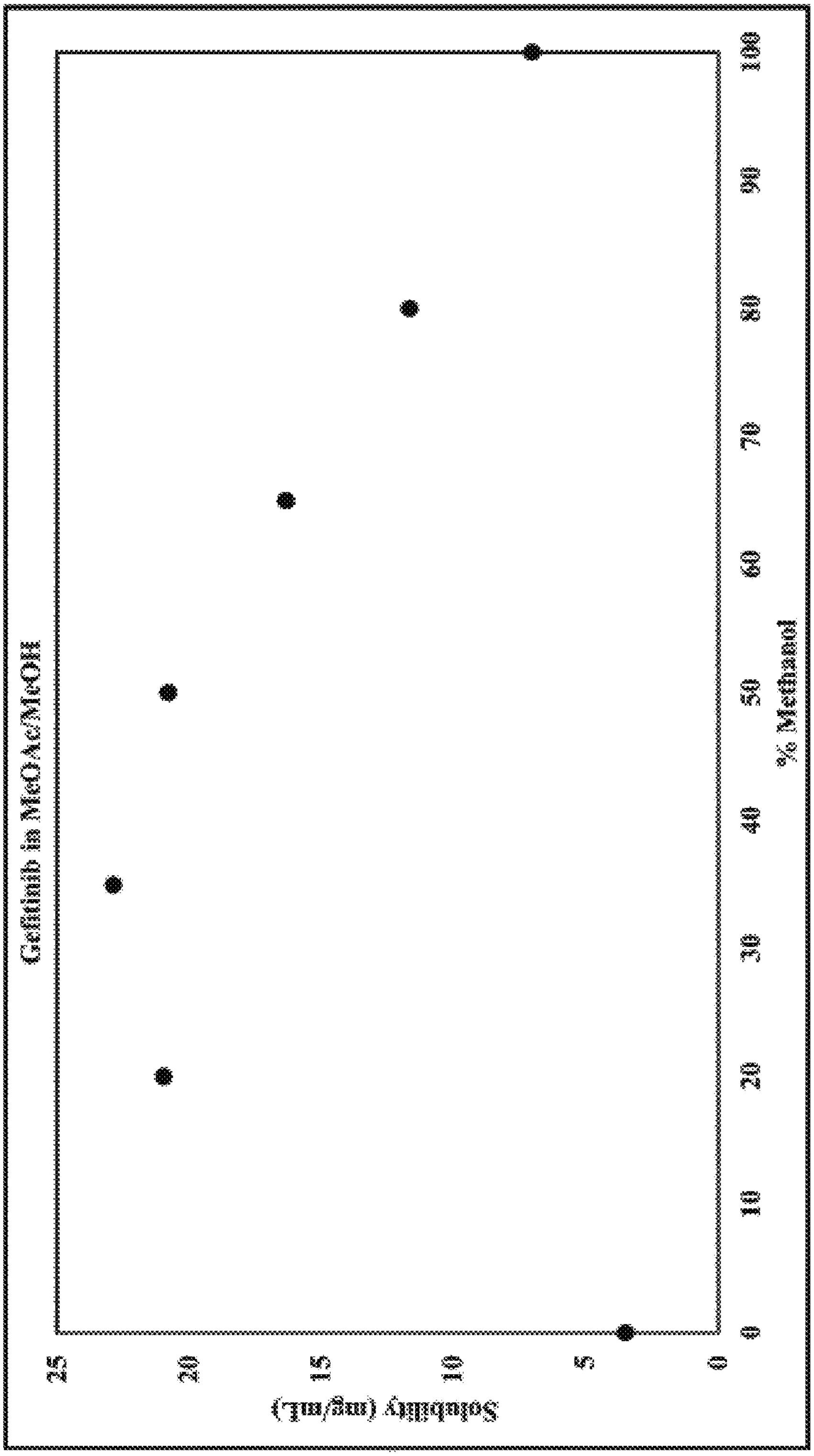
FIG. 10: graphically presentation of the data of table 5: Solubility in mg/ml, the saturation concentration of Gefitinib in MeOAc/MeOH.

FIG. 10 shows a graphically presentation of the data of table 5: Solubility in mg/ml.

TABLE 5

| Gefitinib | | | | | | | |
|---|---|---|---|---|---|---|---|
| | Solvent Ratio (MeOAc:MeOH) | | | | | | |
| | 100:0 | 80:20 | 65:35 | 50:50 | 35:65 | 20:80 | 0:100 |
| Concentration (wt %) | 0.37 ± 0.01 | 2.32 ± 0.02 | 2.600 ± 0.006 | 2.42 ± 0.03 | 1.950 ± 0.005 | 1.421 ± 0.001 | 0.879 ± 0.005 |

TABLE 5-continued

| Gefitinib | | | | | | | |
|---|---|---|---|---|---|---|---|
| | Solvent Ratio (MeOAc:MeOH) | | | | | | |
| | 100:0 | 80:20 | 65:35 | 50:50 | 35:65 | 20:80 | 0:100 |
| Concentration (mg/mL) | 3.5 ± 0.1 | 20.9 ± 0.2 | 22.85 ± 0.05 | 20.8 ± 0.2 | 16.31 ± 0.04 | 11.61 ± 0.01 | 6.96 ± 0.04 |

Example 2: Solubilities in EtOAc:EtOH

Example 2a: Sulfasalazine

Table 2 shows the saturation concentration of Sulfasalazine in EtOAc/EtOH.

Figure 3:
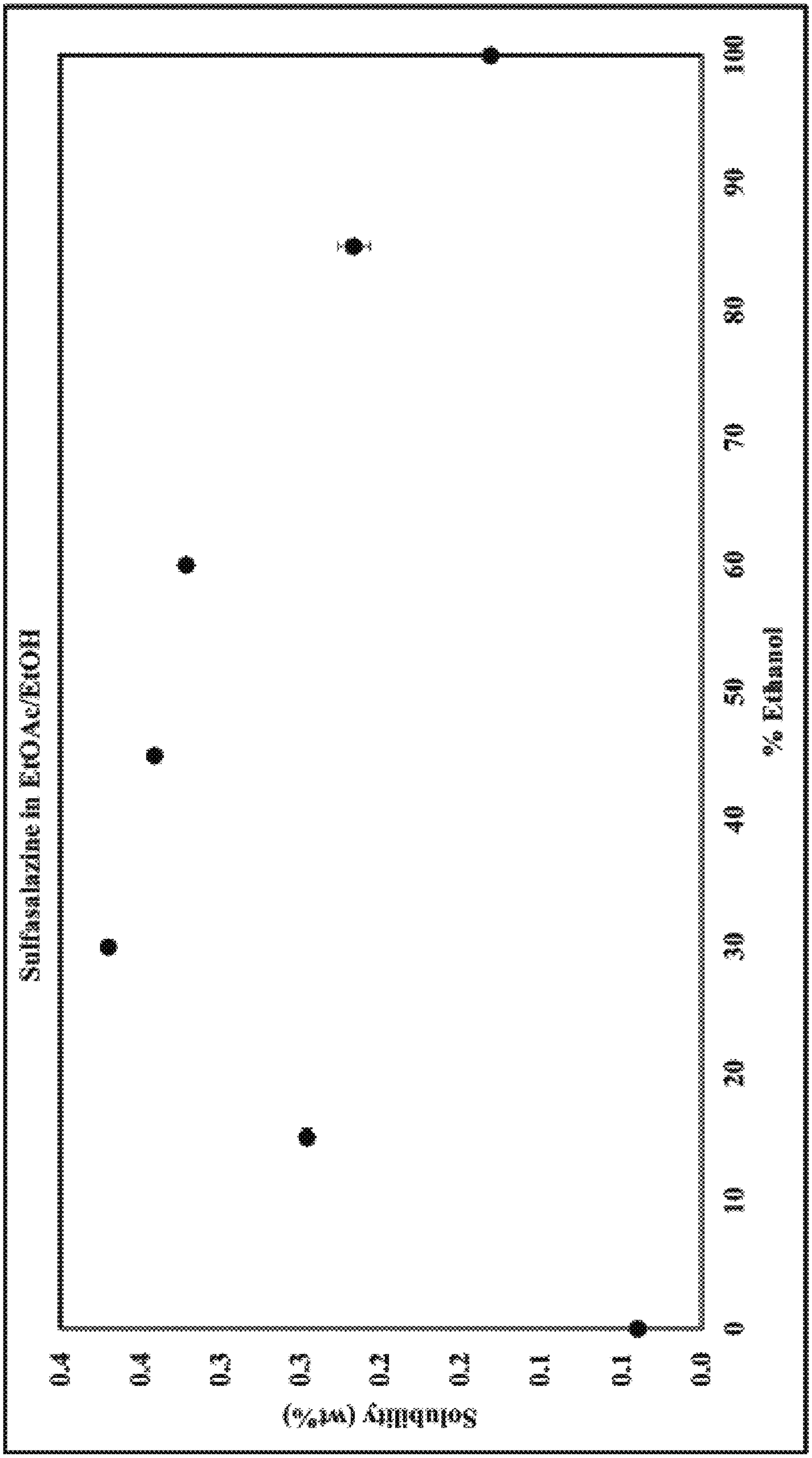
FIG. 3: graphically presentation of the data of table 2: Solubility in wt %, the saturation concentration of Sulfasalazine in EtOAc/EtOH.

FIG. 3 shows a graphically presentation of the data of table 2: Solubility in wt %.

Figure 4:
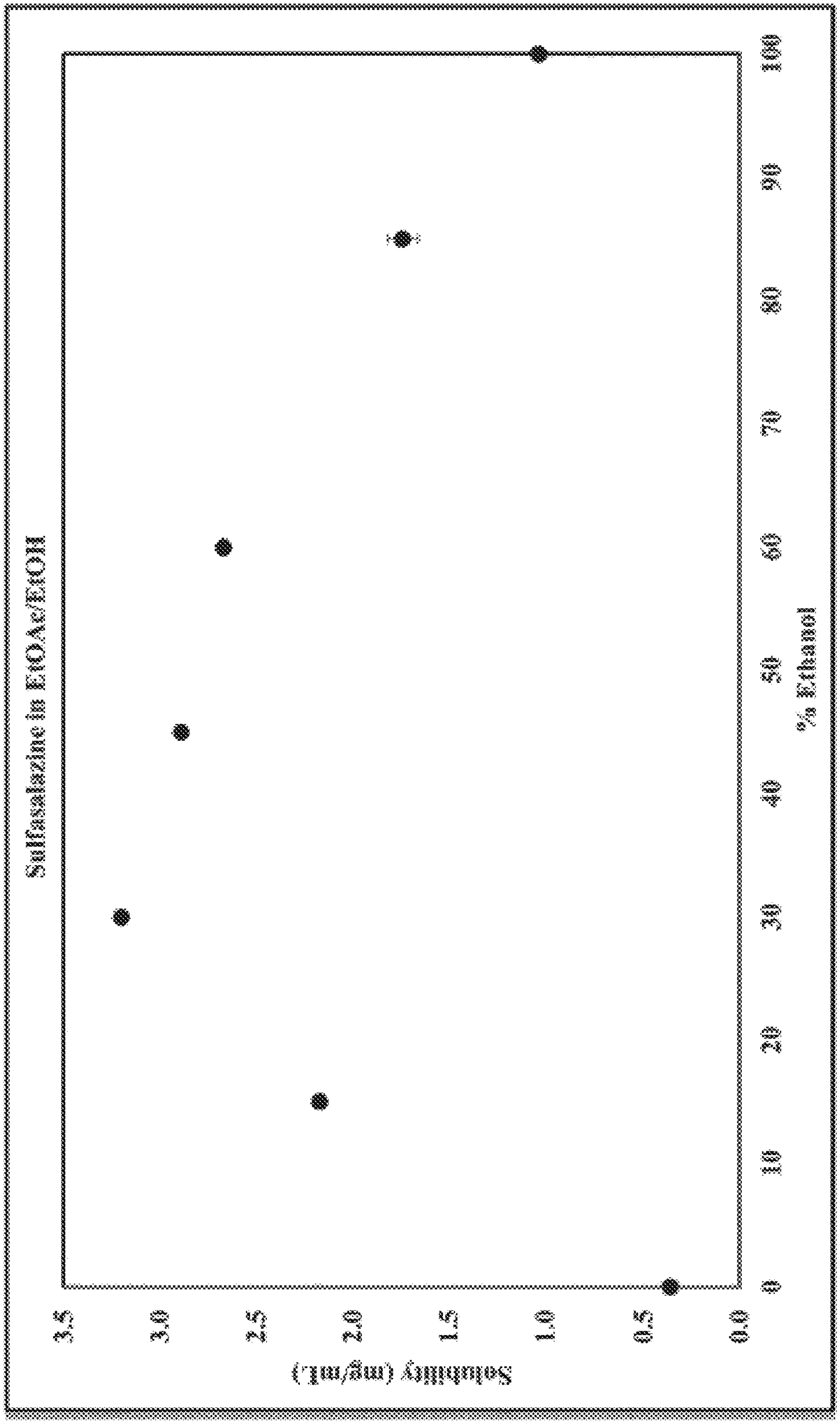
FIG. 4: graphically presentation of the data of table 2: Solubility in mg/ml, the saturation concentration of Sulfasalazine in EtOAc/EtOH.

FIG. 4 shows a graphically presentation of the data of table 2: Solubility in mg/ml.

TABLE 2

| Sulfasalazine | | | | | | | |
|---|---|---|---|---|---|---|---|
| | Solvent Ratio (EtOAc:EtOH) | | | | | | |
| | 100:0 | 85:15 | 70:30 | 55:45 | 40:60 | 15:85 | 0:100 |
| Concentration (wt %) | 0.040 ± 0.004 | 0.246 ± 0.003 | 0.370 ± 0.002 | 0.341 ± 0.003 | 0.321 ± 0.001 | 0.22 ± 0.01 | 0.130 ± 0.001 |
| Concentration (mg/mL) | 0.36 ± 0.04 | 2.17 ± 0.03 | 3.20 ± 0.02 | 2.89 ± 0.03 | 2.67 ± 0.01 | 1.74 ± 0.08 | 1.03 ± 0.01 |

Example 2b: Nilotinib

Table 4 shows the saturation concentration of Nilotinib in EtOAc/EtOH.

Figure 7:
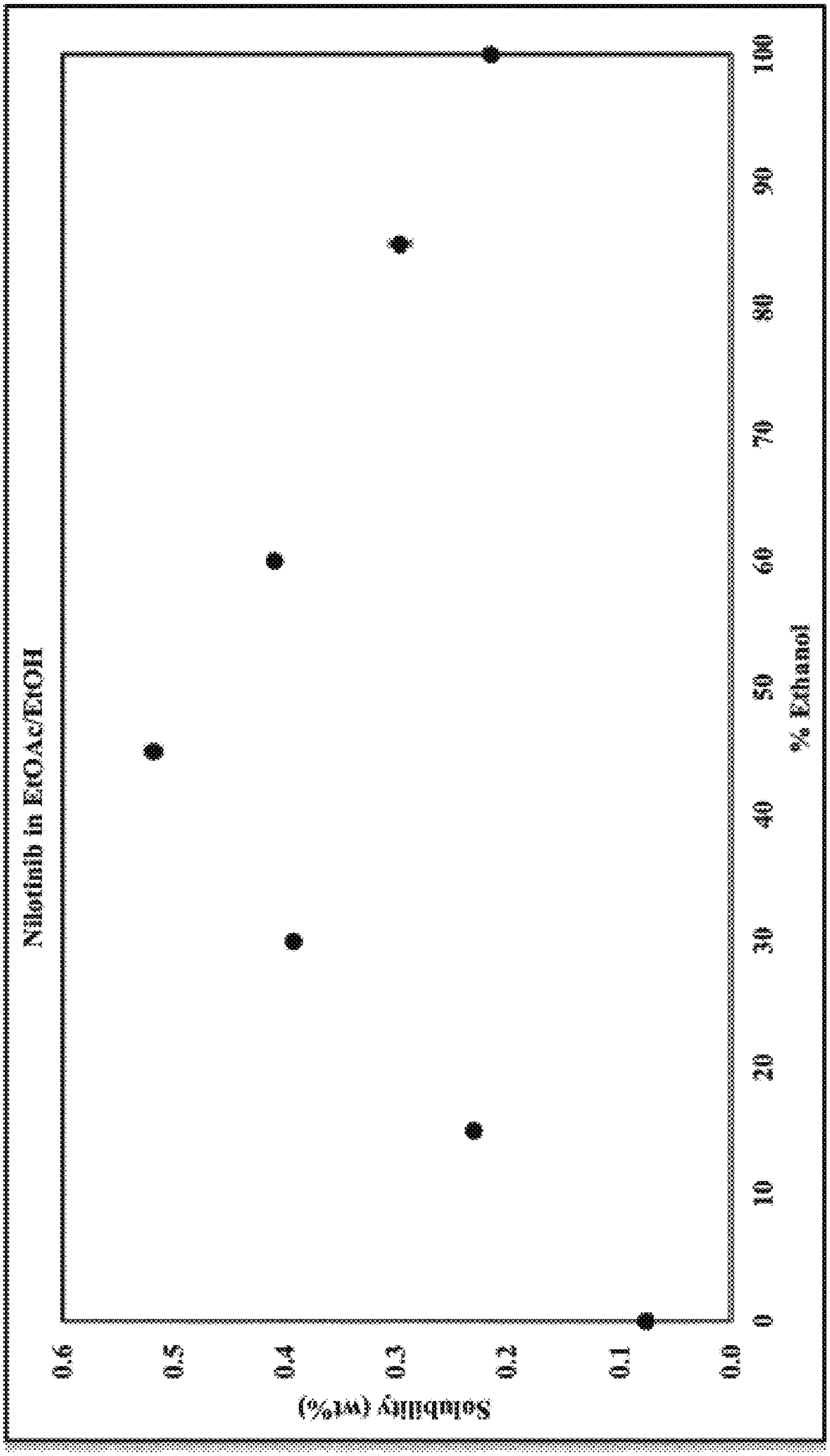
FIG. 7: graphically presentation of the data of table 4: Solubility in wt %, the saturation concentration of Nilotinib in EtOAc/EtOH.

FIG. 7 shows a graphically presentation of the data of table 4: Solubility in wt %.

Figure 8:
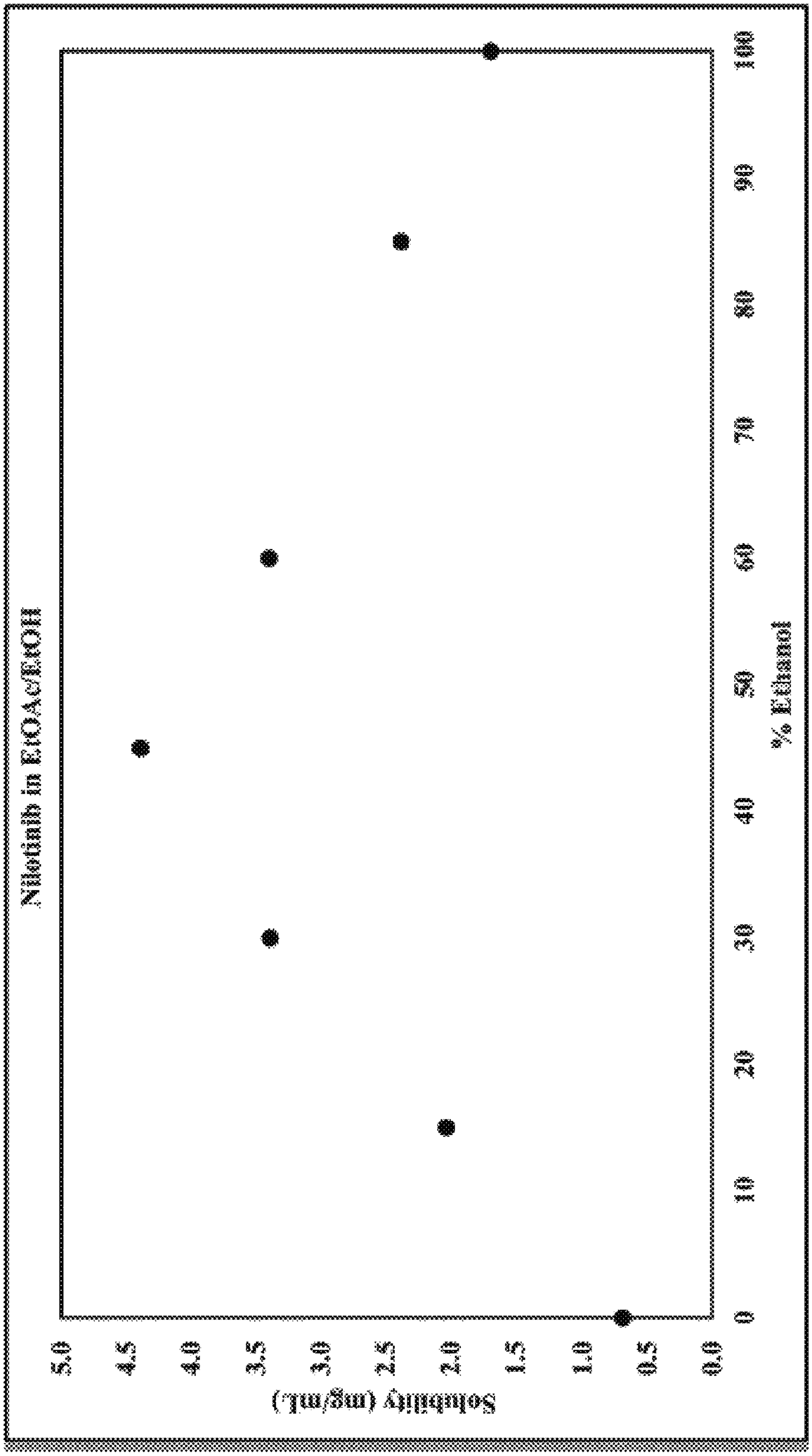
FIG. 8: graphically presentation of the data of table 4: Solubility in mg/ml, the saturation concentration of Nilotinib in EtOAc/EtOH.

FIG. 8 shows a graphically presentation of the data of table 4: Solubility in mg/ml.

TABLE 4

| Nilotinib | | | | | | | |
|---|---|---|---|---|---|---|---|
| | Solvent Ratio (EtOAc:EtOH) | | | | | | |
| | 100:0 | 85:15 | 70:30 | 55:45 | 40:60 | 15:85 | 0:100 |
| Concentration (wt %) | 0.076 ± 0.001 | 0.230 ± 0.003 | 0.392 ± 0.001 | 0.518 ± 0.008 | 0.408 ± 0.002 | 0.30 ± 0.01 | 0.214 ± 0.001 |
| Concentration (mg/mL) | 0.69 ± 0.01 | 2.03 ± 0.03 | 3.39 ± 0.01 | 4.69 ± 0.07 | 3.40 ± 0.02 | 2.38 ± 0.08 | 1.69 ± 0.01 |

Example 2c: Gefitinib

Table 6 shows the saturation concentration of Gefitinib in EtOAc/EtOH.

Figure 11:
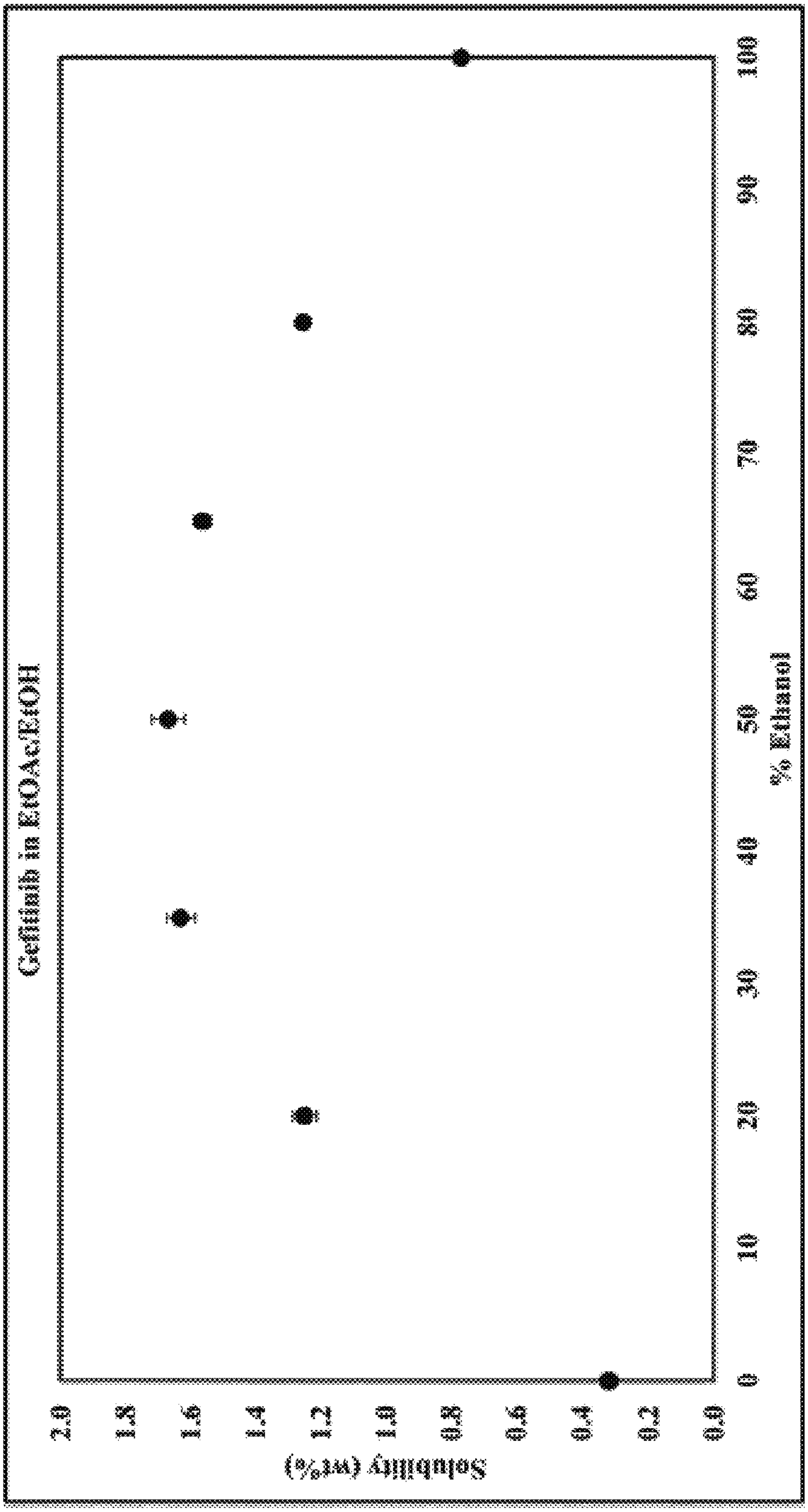
FIG. 11: graphically presentation of the data of table 6: Solubility in wt %, the saturation concentration of Gefitinib in EtOAc/EtOH.

FIG. 11 shows a graphically presentation of the data of table 6: Solubility in wt %.

Figure 12:
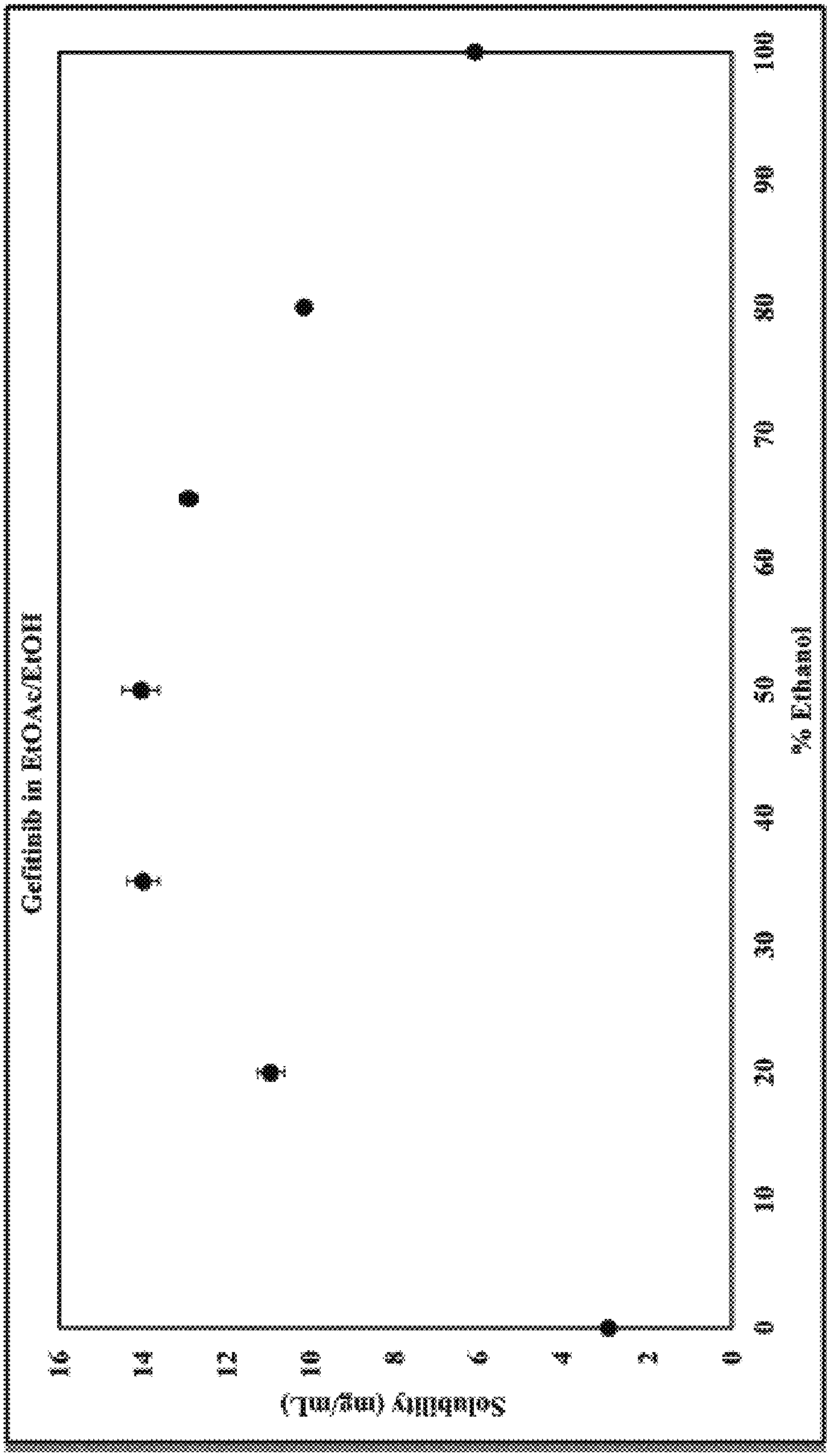
FIG. 12: graphically presentation of the data of table 6: Solubility in mg/ml, the saturation concentration of Gefitinib in EtOAc/EtOH.

FIG. 12 shows a graphically presentation of the data of table 6: Solubility in mg/ml.

TABLE 6

| Gefitinib | | | | | | | |
|---|---|---|---|---|---|---|---|
| | Solvent Ratio (EtOAc:EtOH) | | | | | | |
| | 100:0 | 80:20 | 65:35 | 50:50 | 35:65 | 20:80 | 0:100 |
| Concentration (wt %) | 0.32 ± 0.01 | 1.25 ± 0.04 | 1.63 ± 0.04 | 1.67 ± 0.05 | 1.56 ± 0.03 | 1.25 ± 0.01 | 0.77 ± 0.01 |
| Concentration (mg/mL) | 2.89 ± 0.09 | 11.0 ± 0.3 | 14.0 ± 0.4 | 14.0 ± 0.4 | 12.9 ± 0.2 | 10.2 ± 0.1 | 6.07 ± 0.08 |

Example 3: Solubilities in MeOAc:EtOH

Example 3a: Gefitinib

Table 7 shows the saturation concentration of Gefitinib in MeOAc/EtOH.

Figure 13:
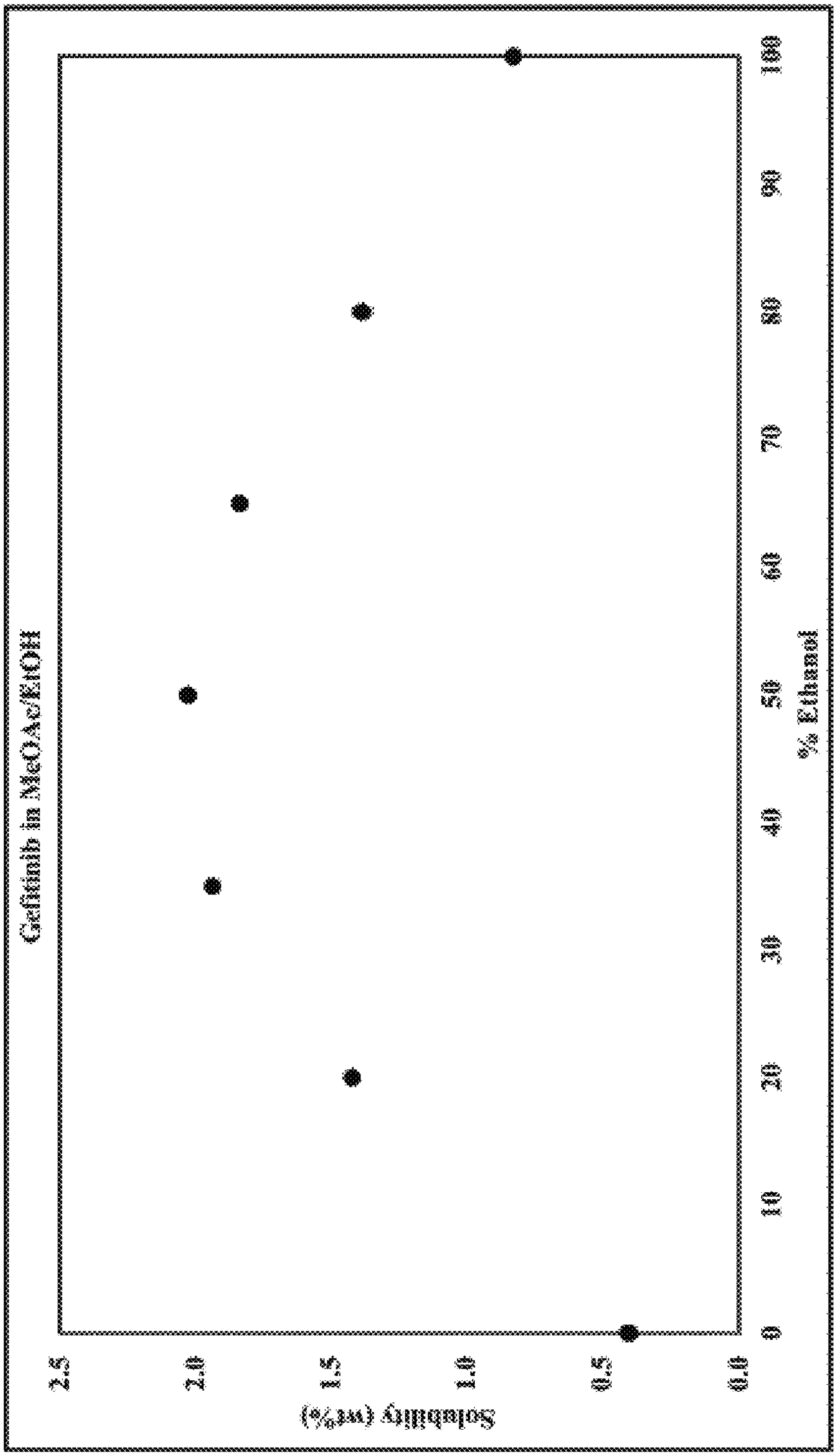
FIG. 13: graphically presentation of the data of table 7: Solubility in wt %, the saturation concentration of Gefitinib in MeOAc/EtOH.

FIG. 13 shows a graphically presentation of the data of table 7: Solubility in wt %.

Figure 14:
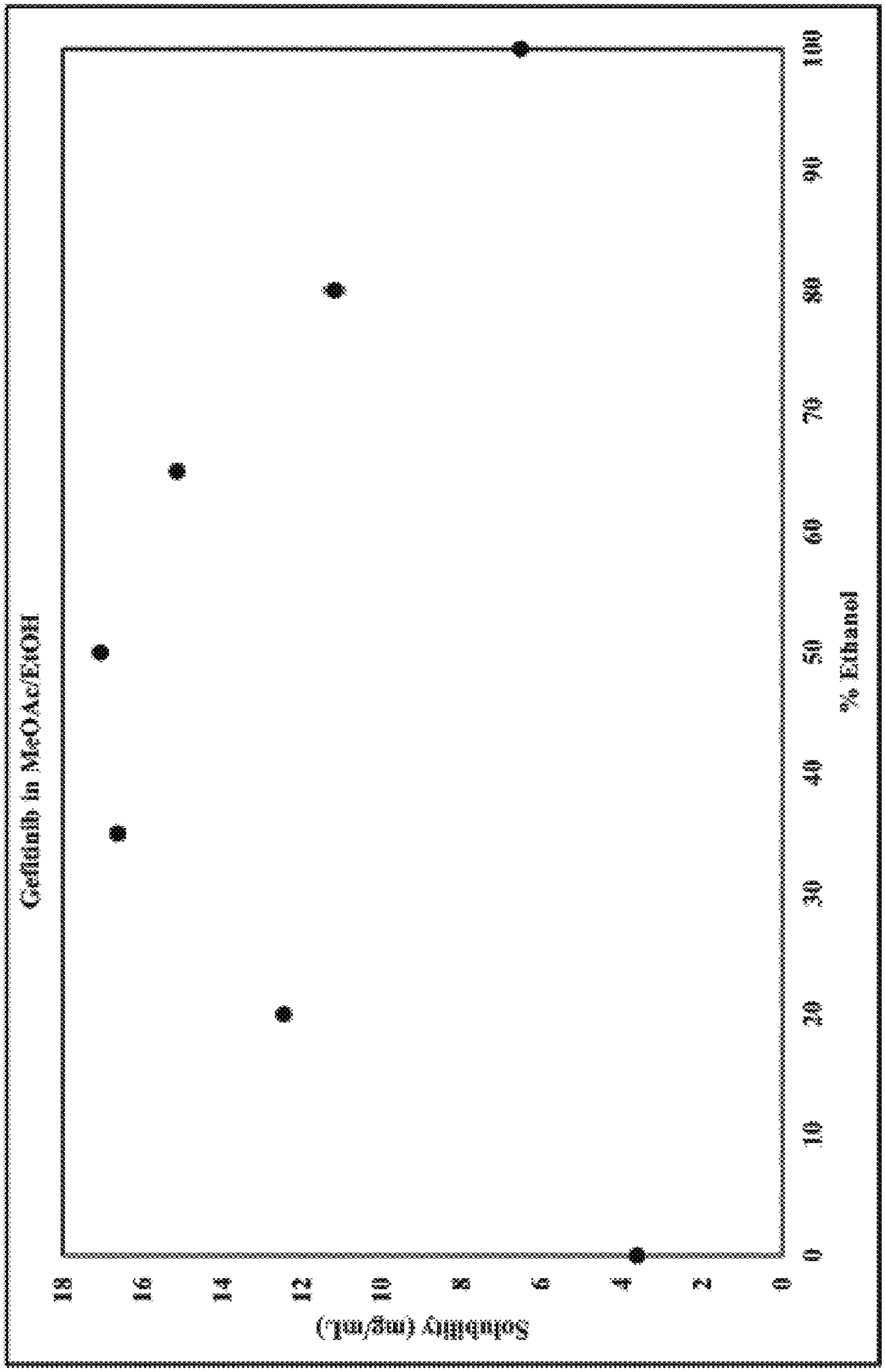
FIG. 14: graphically presentation of the data of table 7: Solubility in mg/ml, the saturation concentration of Gefitinib in MeOAc/EtOH.

FIG. 14 shows a graphically presentation of the data of table 7: Solubility in mg/ml.

TABLE 7

| Gefitinib | | | | | | | |
|---|---|---|---|---|---|---|---|
| | Solvent Ratio (MeOAc:EtOH) | | | | | | |
| | 100:0 | 80:20 | 65:35 | 50:50 | 35:65 | 20:80 | 0:100 |
| Concentration (wt %) | 0.402 ± 0.003 | 1.419 ± 0.008 | 1.93 ± 0.02 | 2.025 ± 0.005 | 1.83 ± 0.02 | 1.38 ± 0.02 | 0.824 ± 0.005 |
| Concentration (mg/mL) | 3.63 ± 0.03 | 12.45 ± 0.07 | 16.6 ± 0.2 | 14.04 ± 0.05 | 15.1 ± 0.1 | 11.2 ± 0.3 | 6.50 ± 0.05 |

Example 4: Solubilities in EtOAc:MeOH

Example 4a: Gefitinib

Table 8 shows the saturation concentration of Gefitinib in EtOAc/MeOH.

Figure 15:
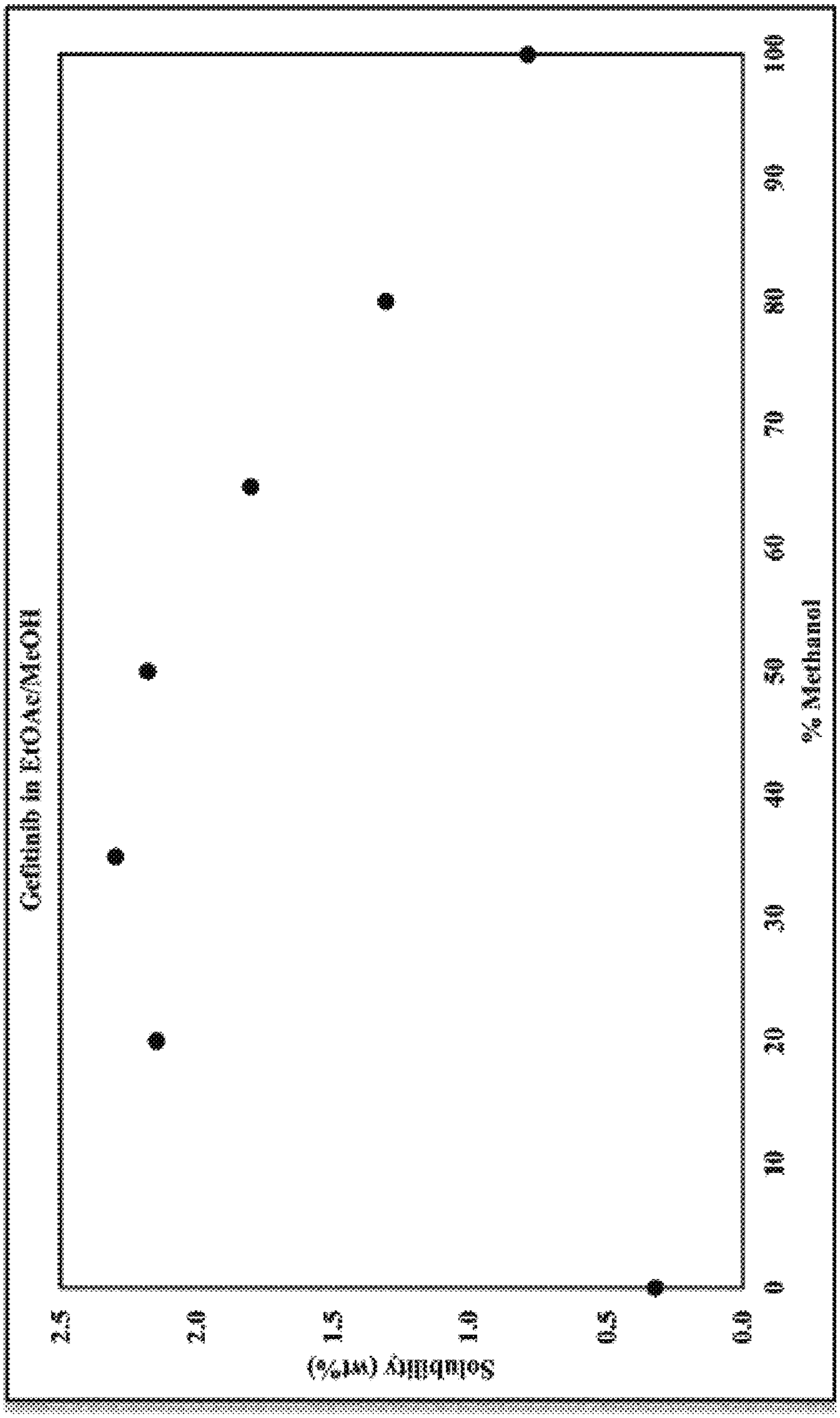
FIG. 15: graphically presentation of the data of table 8: Solubility in wt %, the saturation concentration of Gefitinib in EtOAc/MeOH.

FIG. 15 shows a graphically presentation of the data of table 8: Solubility in wt %.

Figure 16:
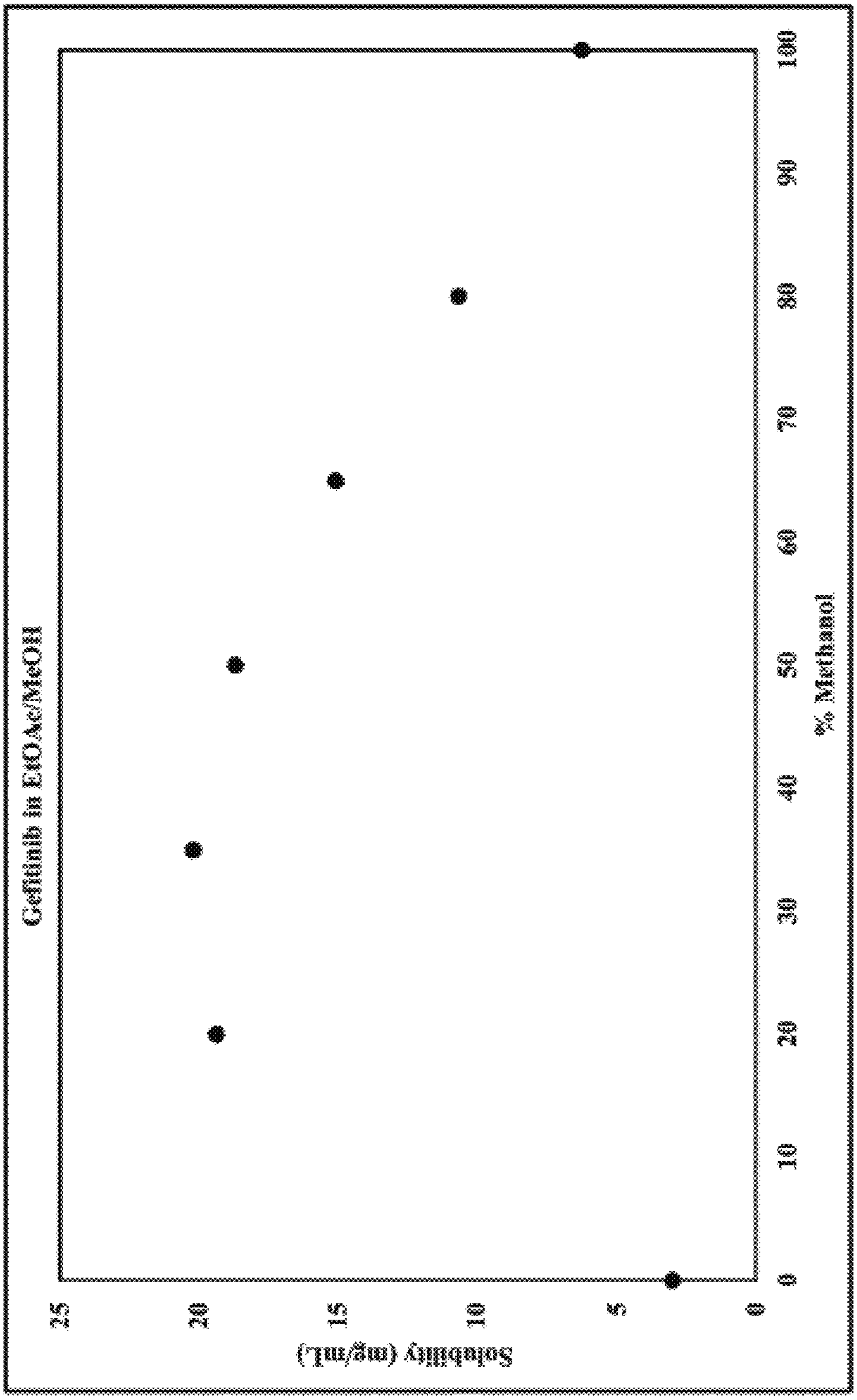
FIG. 16: graphically presentation of the data of table 8: Solubility in mg/ml, the saturation concentration of Gefitinib in EtOAc/MeOH.

FIG. 16 shows a graphically presentation of the data of table 8: Solubility in mg/ml.

TABLE 8

| Gefitinib | | | | | | | |
|---|---|---|---|---|---|---|---|
| | Solvent Ratio (EtOAc:MeOH) | | | | | | |
| | 100:0 | 80:20 | 65:35 | 50:50 | 35:65 | 20:80 | 0:100 |
| Concentration (wt %) | 0.323 ± 0.001 | 2.147 ± 0.01 | 2.297 ± 0.007 | 2.179 ± 0.007 | 1.80 ± 0.01 | 1.30 ± 0.01 | 0.783 ± 0.005 |
| Concentration (mg/mL) | 3.01 ± 0.01 | 19.4 ± 0.1 | 20.19 ± 0.06 | 18.68 ± 0.06 | 15.1 ± 0.1 | 10.6 ± 0.01 | 6.20 ± 0.04 |

Example 5: Solubilities in EtFormate:MeOH

Example 5a: Gefitinib

Table 9 shows the saturation concentration of Gefitinib in EtFormate/MeOH.

Figure 17:
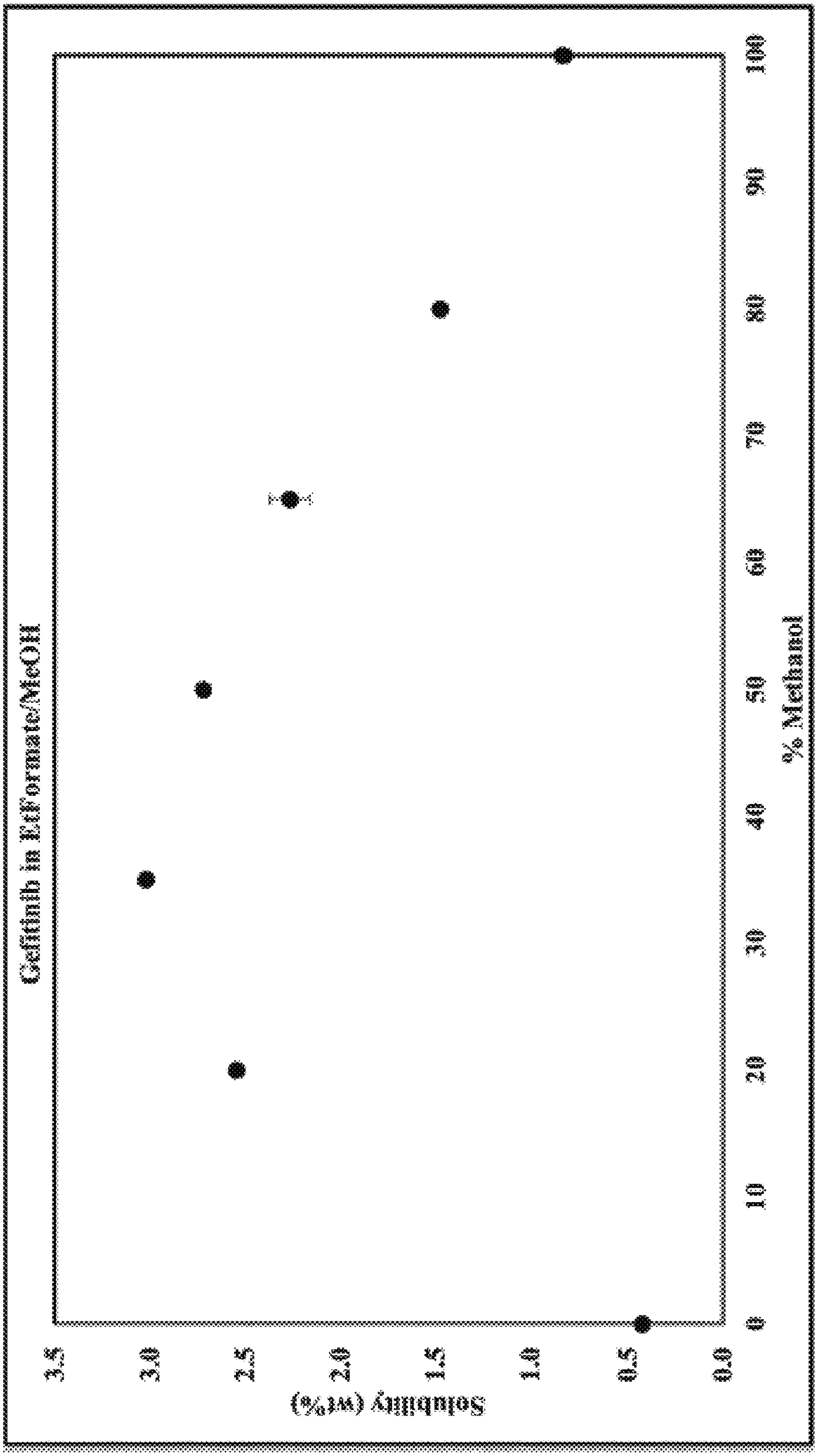
FIG. 17: graphically presentation of the data of table 9: Solubility in wt %, the saturation concentration of Gefitinib in EtFormate/MeOH.

FIG. 17 shows a graphically presentation of the data of table 9: Solubility in wt %.

Figure 18:
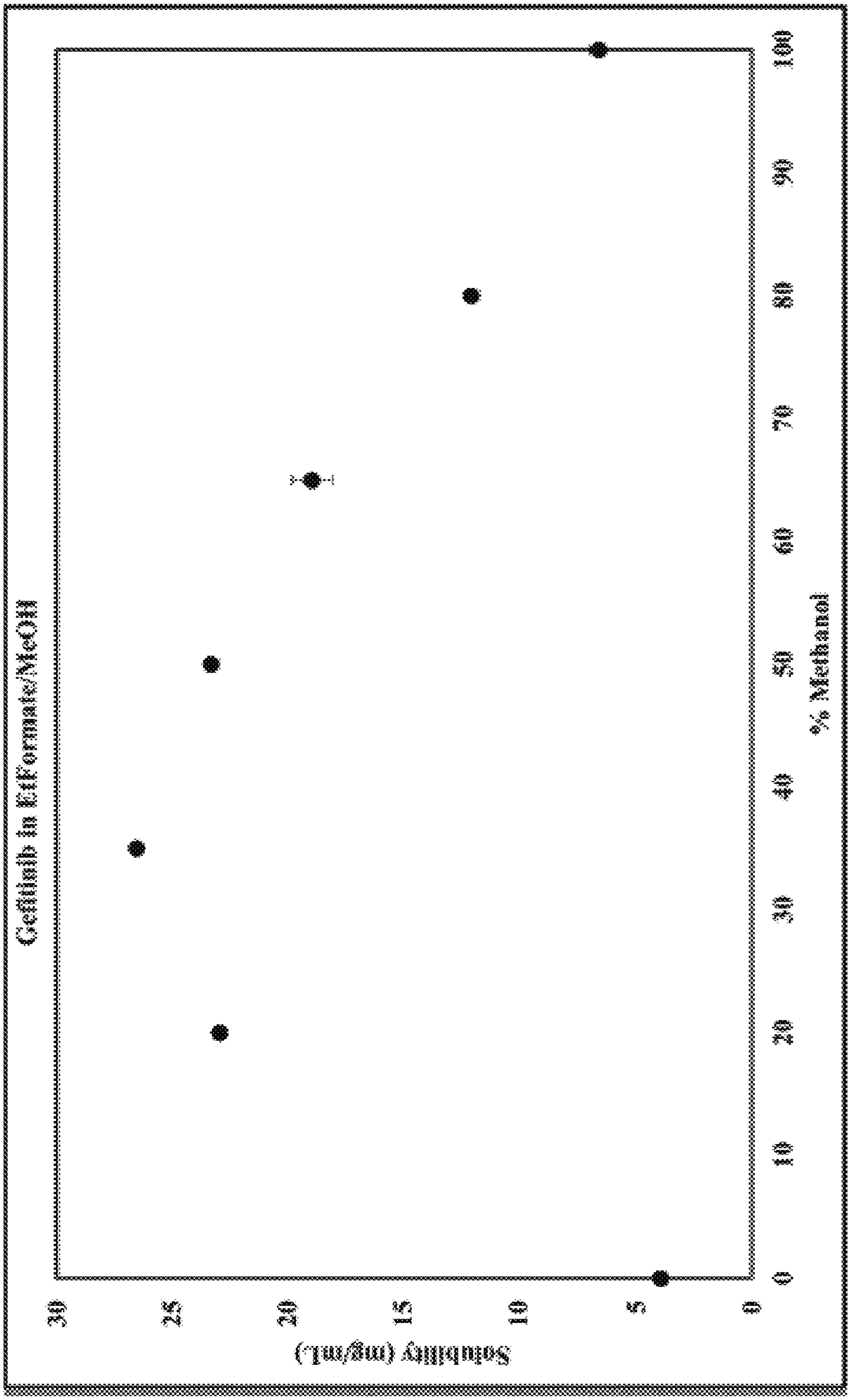
FIG. 18: graphically presentation of the data of table 9: Solubility in mg/ml, the saturation concentration of Gefitinib in EtFormate/MeOH.

FIG. 18 shows a graphically presentation of the data of table 9: Solubility in mg/ml.

TABLE 9

| Gefitinib | | | | | | | |
|---|---|---|---|---|---|---|---|
| | Solvent Ratio (EtFor:MeOH) | | | | | | |
| | 100:0 | 80:20 | 65:35 | 50:50 | 35:65 | 20:80 | 0:100 |
| Concentration (wt %) | 0.422 ± 0.006 | 2.54 ± 0.02 | 3.02 ± 0.02 | 2.70 ± 0.03 | 2.3 ± 0.1 | 1.47 ± 0.04 | 0.833 ± 0.009 |
| Concentration (mg/mL) | 3.94 ± 0.05 | 22.9 ± 0.1 | 26.5 ± 0.1 | 23.3 ± 0.3 | 28.9 ± 0.9 | 12.0 ± 0.3 | 6.60 ± 0.07 |

Example 6: Solubilities in MeOAc/MeOH with 20% Water

Example 6a: Gefitinib

Table 10 shows the saturation concentration of Gefitinib in MeOAc/MeOH with 2000 water, the wt %0 being based on the weight of mixed solvent, that is on the combined weight of solvent 1, solvent 2 and water.

Figure 29:
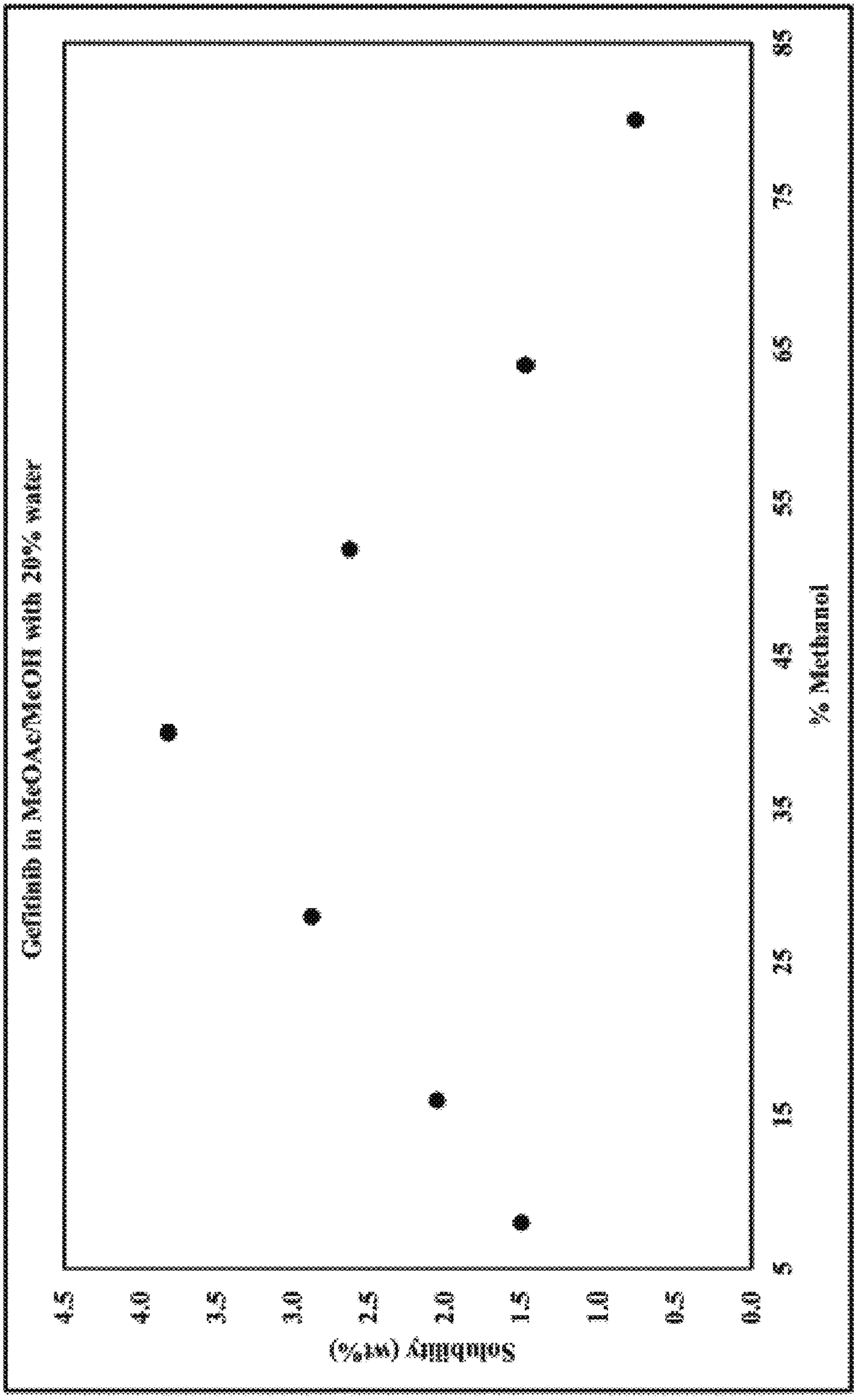
FIG. 29: graphically presentation of the data of table 10: Solubility in wt %, the saturation concentration of Gefitinib in MeOAc/MeOH with 20% water.

FIG. 29 shows a graphically presentation of the data of table 10: Solubility in wt %.

Figure 30:
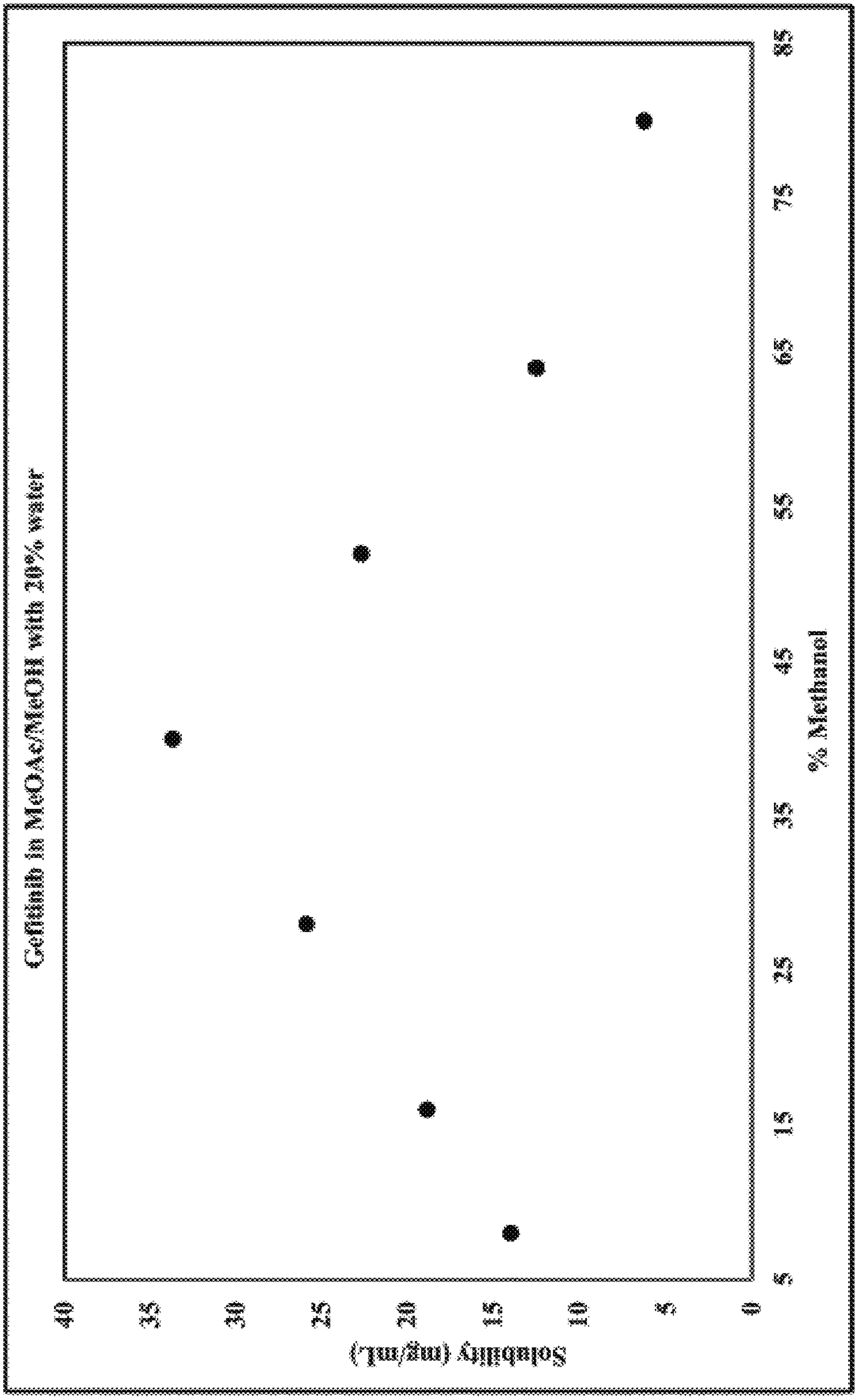
FIG. 30: graphically presentation of the data of table 10: Solubility in mg/ml, the saturation concentration of Gefitinib in MeOAc/MeOH with 20% water.

FIG. 30 shows a graphically presentation of the data of table 10: Solubility in mg/ml.

TABLE 10

| Gefitinib | | | | | | | |
|---|---|---|---|---|---|---|---|
| | Solvent Ratio (MeOAc:MeOH:water) | | | | | | |
| | 72:8:20 | 64:16:20 | 52:28:20 | 40:40:20 | 28:52:20 | 16:64:20 | 0:80:20 |
| Concentration (wt %) | 1.494 ± 0.009 | 2.046 ± 0.003 | 2.87 ± 0.01 | 3.82 ± 0.02 | 2.62 ± 0.01 | 1.47 ± 0.05 | 0.759 ± 0.001 |
| Concentration (mg/mL) | 13.93 ± 0.08 | 18.81 ± 0.02 | 25.8 ± 0.1 | 33.7 ± 0.2 | 22.7 ± 0.1 | 12.4 ± 0.5 | 6.27 ± 0.01 |

Overlay of Figures—Sulfasalazine

Figure 19:
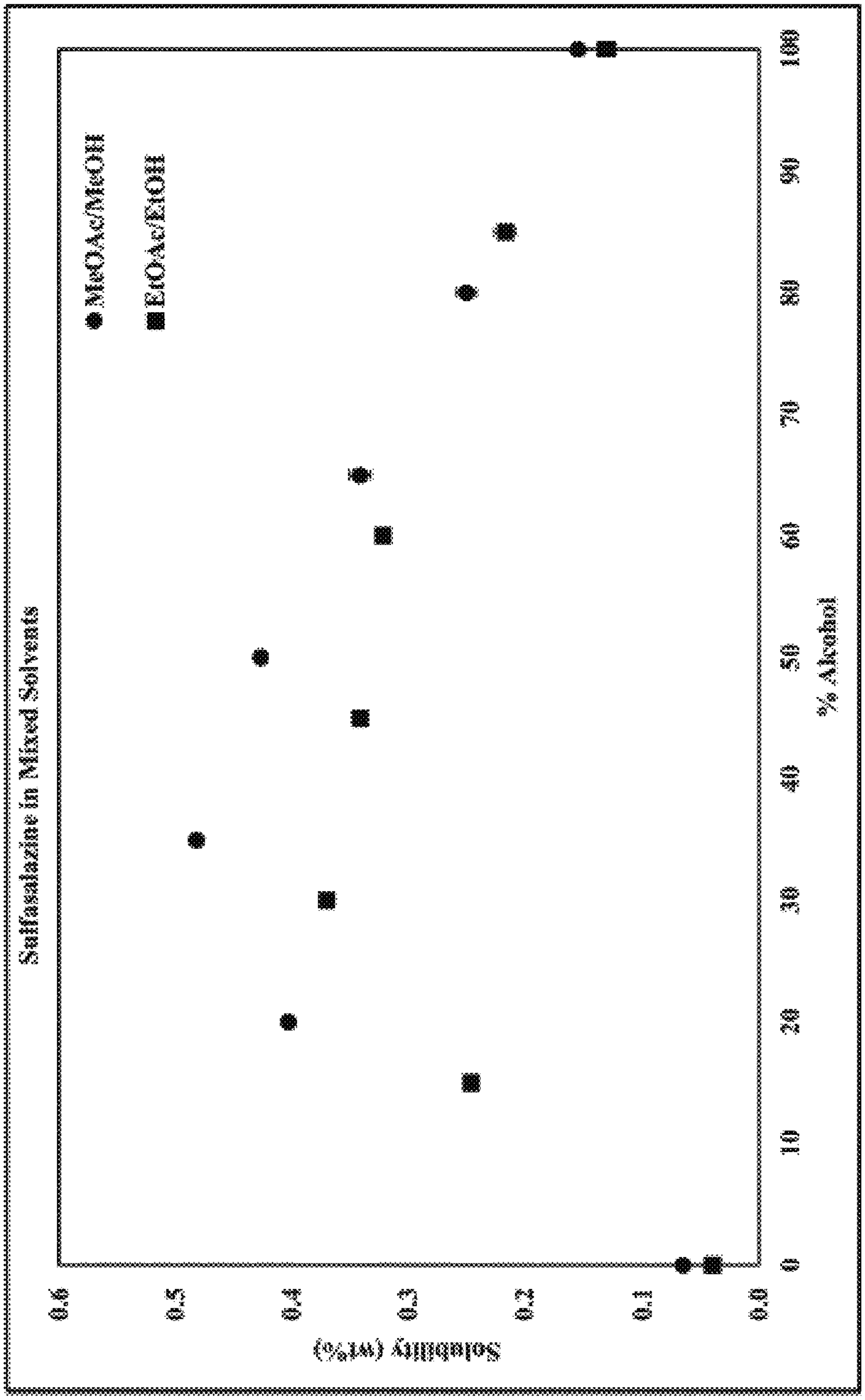
FIG. 19: overlay of the FIGS. 1 and 3.

FIG. 19 shows an overlay of the FIGS. 1 and 3.

Figure 20:
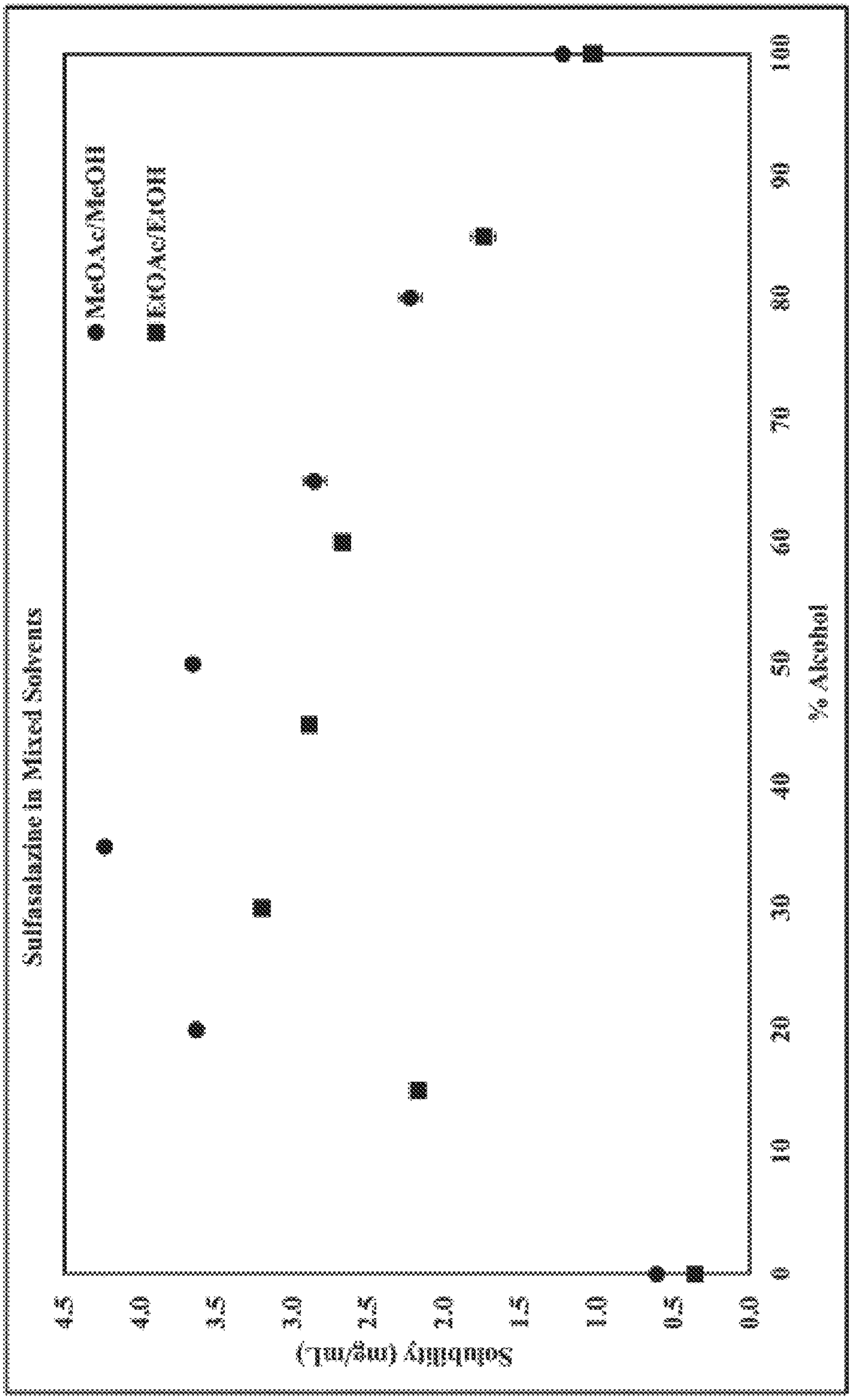
FIG. 20: overlay of the FIGS. 2 and 4.

FIG. 20 shows an overlay of the FIGS. 2 and 4.

Overlay of Figures—Nilotinib

Figure 21:
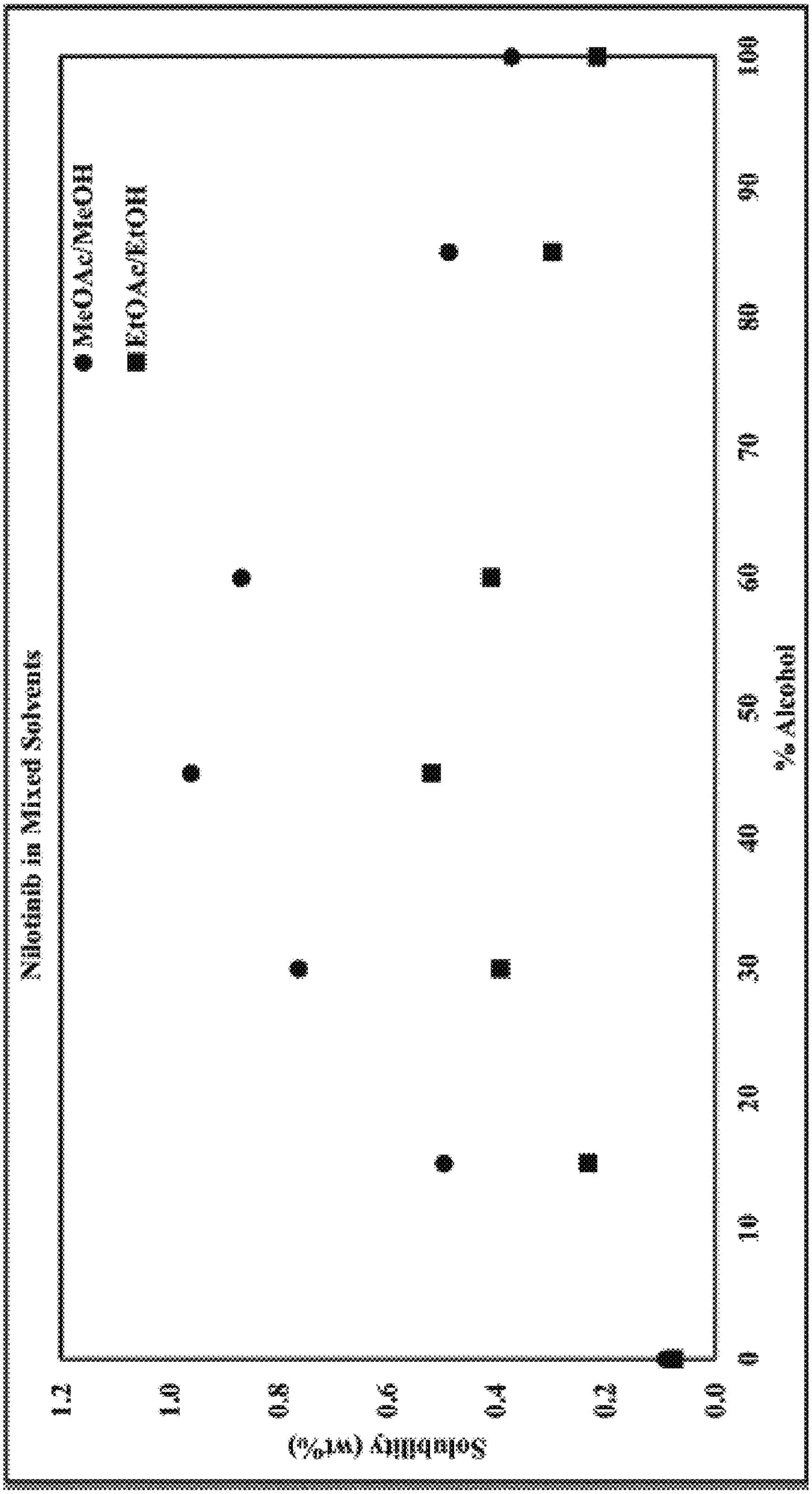
FIG. 21: overlay of the FIGS. 5 and 7.

FIG. 21 shows an overlay of the FIGS. 5 and 7.

Figure 22:
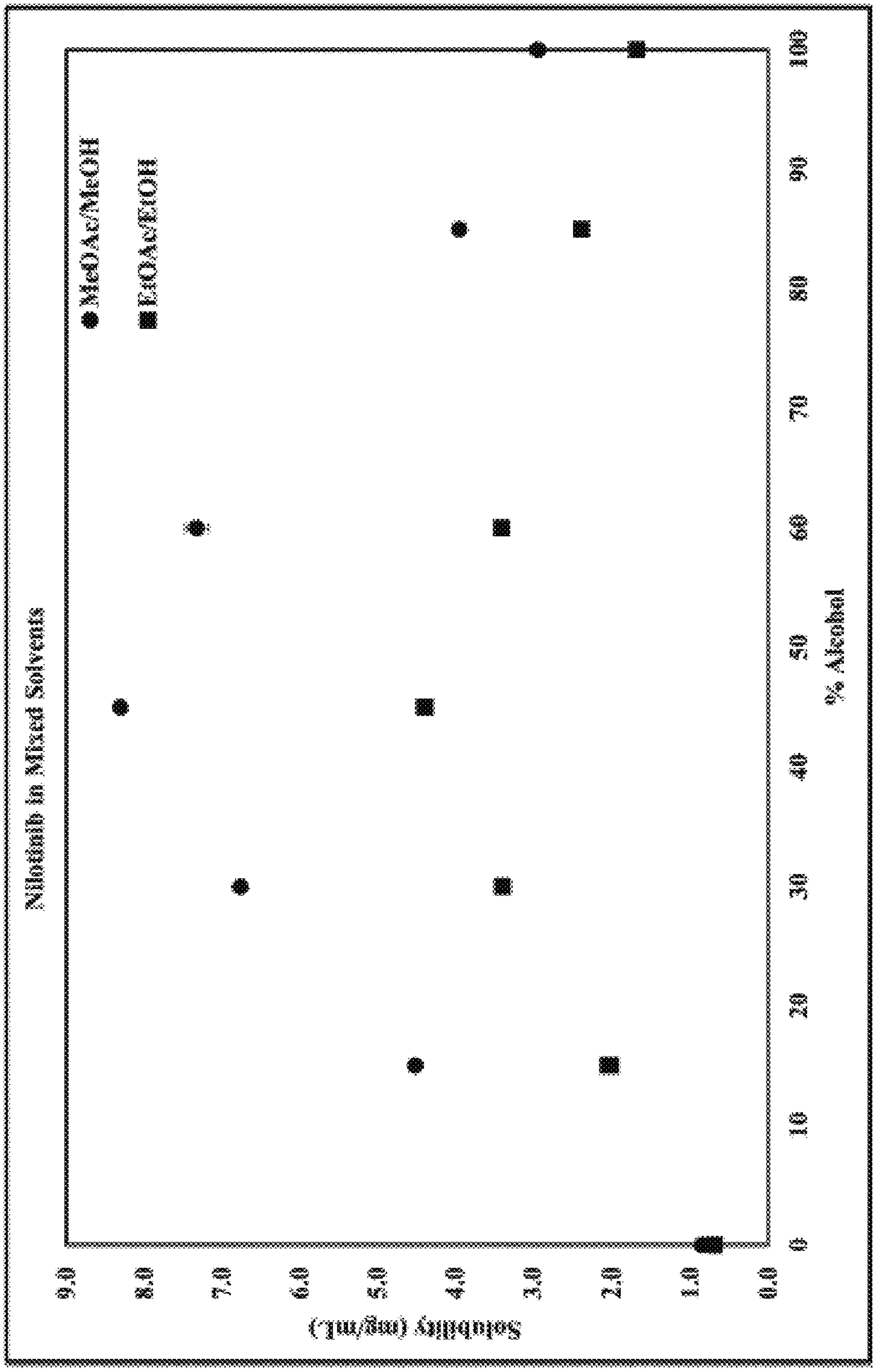
FIG. 22: overlay of the FIGS. 6 and 8.

FIG. 22 shows an overlay of the FIGS. 6 and 8.

Overlay of Figures—Gefitinib

Figure 23:
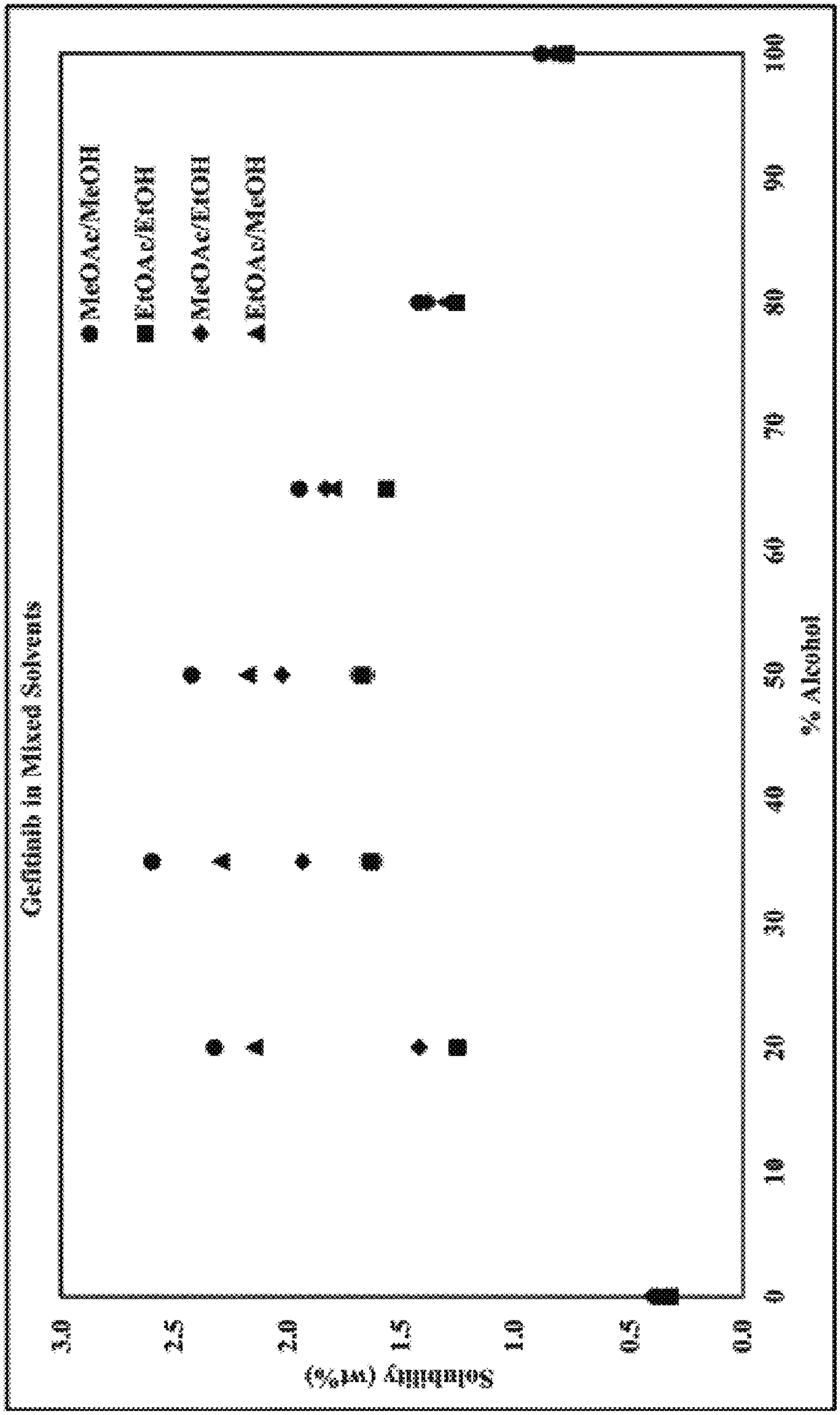
FIG. 23: overlay of the FIGS. 9, 11, 13 and 15.

FIG. 23 shows an overlay of the FIGS. 9, 11, 13 and 15.

Figure 24:
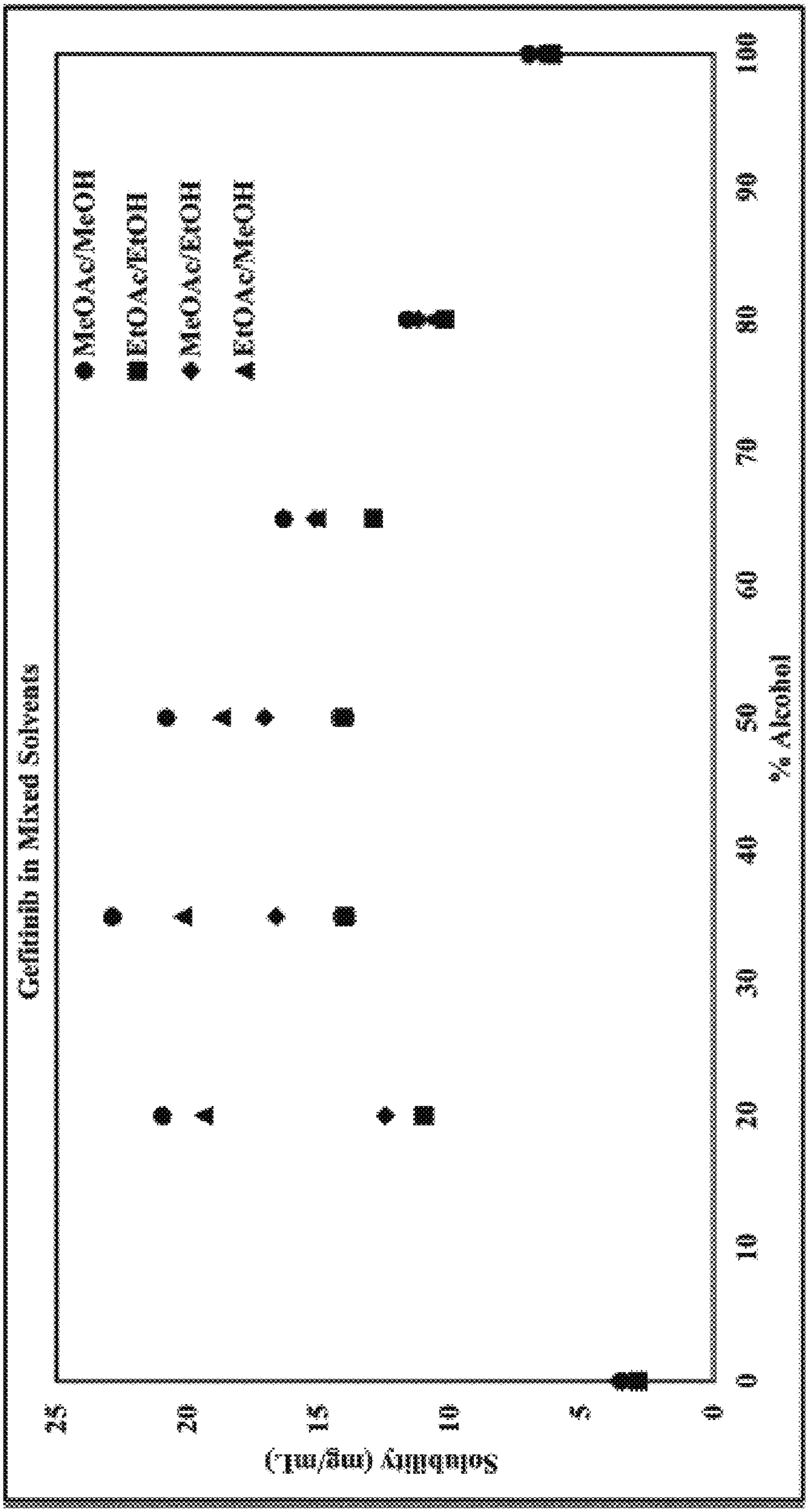
FIG. 24: overlay of the FIGS. 10, 12, 14 and 16.

FIG. 24 shows an overlay of the FIGS. 10, 12, 14 and 16.

Example 7: ASD Using MeOAc/MeOH Mixture—25:75 Gefitinib:PVPVA64

71.4 g of 50/50 (w/w) methanol/methyl acetate was weighed into a flask. 1.01 g of gefitinib was added to the mixed solvent and stirred with a magnetic stir bar at 20° C. until completely dissolved. 3.00 g of PVPVA64 was added and the mixture was stirred for at least 30 min until the polymer was dissolved.

Then the solution was spray dried using a custom built spray dryer. The solution was pumped into a lab-scale 0.3 m diameter stainless steel spray drying chamber using head pressure on the tank of 120 psi. The spray solution was atomized using the nozzle:

1.5 pressure-swirl nozzle with 0.15 mm diameter; SCHLICK Hollow-Cone, model 121 with normal spray cone, Schlick Americas, Bluffton, South Carolina, USA.

Heated nitrogen gas (125 to 130° C. inlet, 48 to 52° C. outlet, 500 g/min) was used to dry the particles. The resulting ASD was collected using a cyclone to separate the solid particles from the gas stream.

The collected ASD was placed in a tray dryer at 40° C./15% RH for secondary drying in order to remove residual solvent. The ASD was dried for 24 h on the tray dryer. The residual amount of MeOH determined by GC was less than 50 ppm after the tray dryer.

Figure 25:
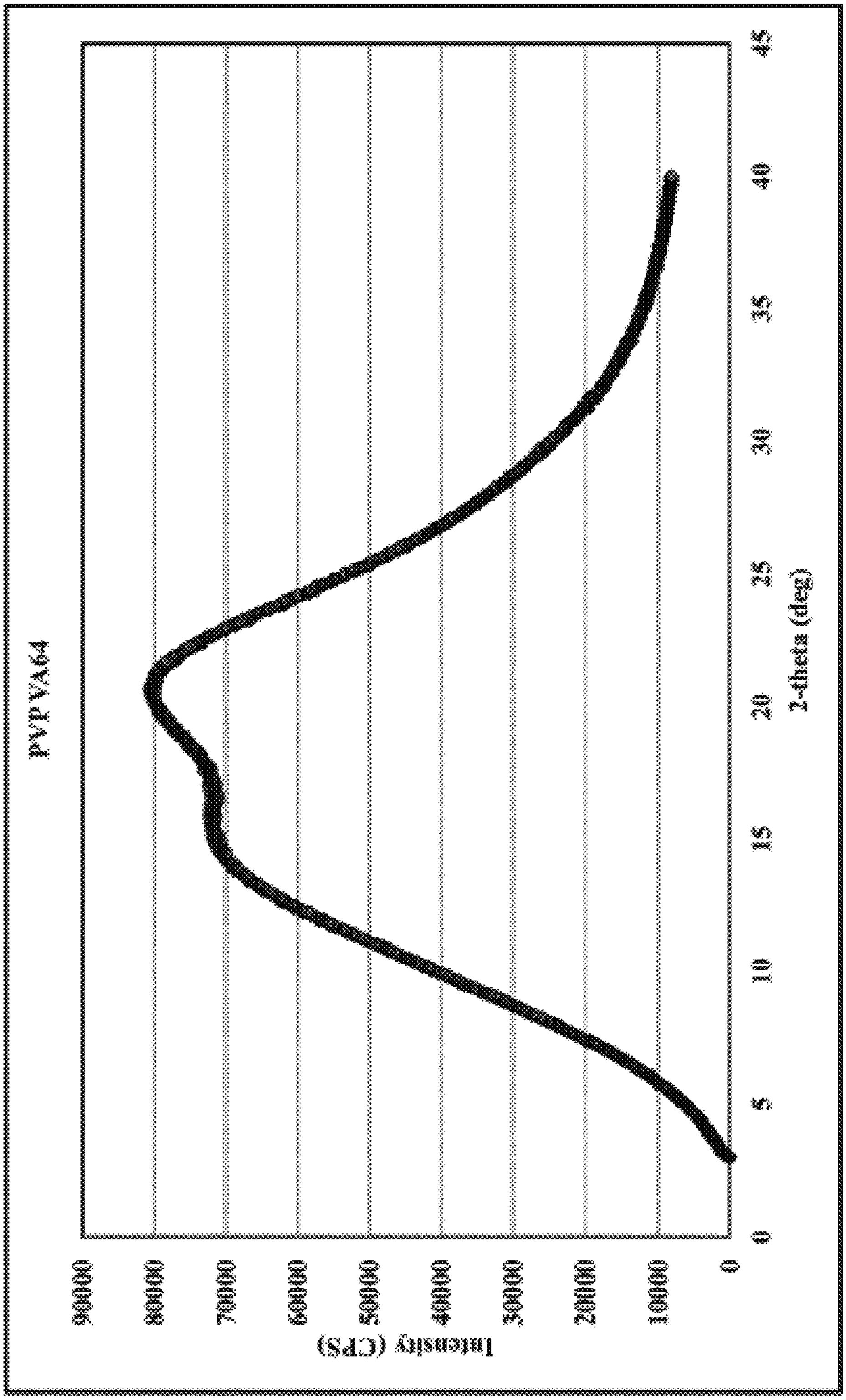
FIG. 25: PXRD of the ASD prepared according to example 7.

FIG. 25 shows the PXRD of the ASD after tray drying. The PXRD shows the ASD to be amorphous as indicated by the lack of sharp diffraction peaks.

Example 8: ASD Using MeOAc/MeOH Mixture—25:75 Gefitinib:Eudragit L100

71.5 g of 50/50 (w/w) methanol/methyl acetate was weighed into a flask. 1.00 g of gefitinib was added to the mixed solvent and stirred with a magnetic stir bar at 20° C. until completely dissolved. 3.01 g of Eudragit L100 was added and the mixture was stirred for at least 30 min until the polymer was dissolved.

Then the solution was spray dried using a custom built spray dryer. The solution was pumped into a lab-scale 0.3 m diameter stainless steel spray drying chamber using head pressure on the tank of 120 psi. The spray solution was atomized using a the nozzle:

1.5 pressure-swirl nozzle with 0.15 mm diameter; SCHLICK Hollow-Cone, model 121 with normal spray cone, Schlick Americas, Bluffton, South Carolina, USA.

Heated nitrogen gas (125 to 130° C. inlet, 48 to 52° C. outlet, 500 g/min) was used to dry the particles. The resulting ASD was collected using a cyclone to separate the solid particles from the gas stream.

The collected ASD was placed in a tray dryer at 40° C./15% RH for secondary drying in order to remove residual solvent. The ASD was dried for 24 h on the tray dryer. The residual amount of MeOH determined by GC was less than 60 ppm after the tray dryer.

Figure 26:
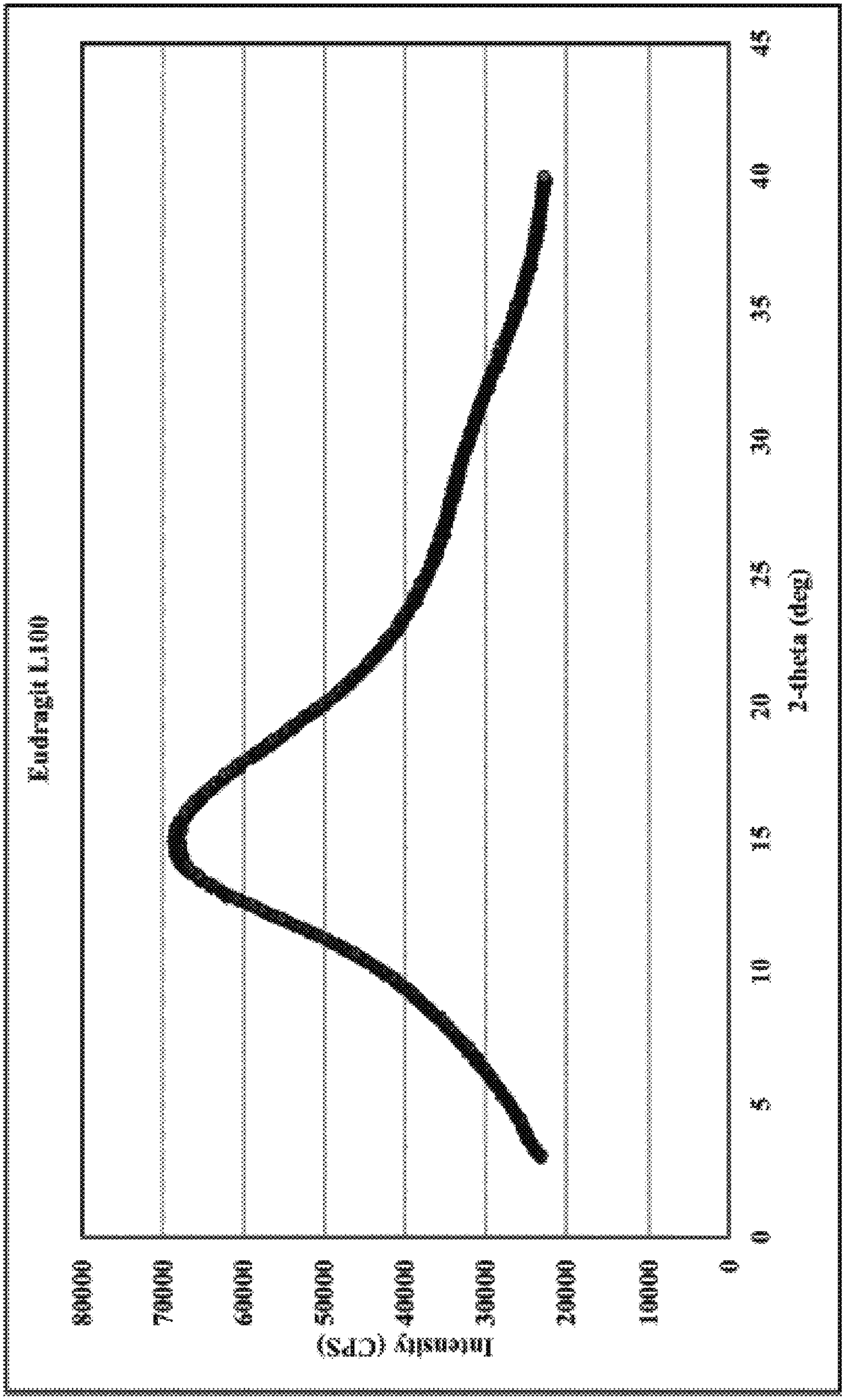
FIG. 26: PXRD of the ASD prepared according to example 8.

FIG. 26 shows the PXRD of the ASD after tray drying. The PXRD shows the ASD to be amorphous as indicated by the lack of sharp diffraction peaks.

Example 9: ASD Using MeOAc/MeOH Mixture—25:75 Gefitinib:HPMCAS-MG 71.5 g of 50/50 (w/w) methanol/methyl acetate was weighed into a flask. 1.00 g of gefitinib was added to the mixed solvent and stirred with a magnetic stir bar at 20° C. until completely dissolved. 3.00 g of HPMCAS-MG was added and the mixture was stirred for at least 30 min until the polymer was dissolved.

Then the solution was spray dried using a custom built spray dryer. The solution was pumped into a lab-scale 0.3 m diameter stainless steel spray drying chamber using head pressure on the tank of 120 psi. The spray solution was atomized using the nozzle:

1.5 pressure-swirl nozzle with 0.15 mm diameter; SCHLICK Hollow-Cone, model 121 with normal spray cone, Schlick Americas, Bluffton, South Carolina, USA.

Heated nitrogen gas (125 to 130° C. inlet, 48 to 52° C. outlet, 500 g/min) was used to dry the particles. The resulting ASD was collected using a cyclone to separate the solid particles from the gas stream.

The collected ASD was placed in a tray dryer at 40° C./15% RH for secondary drying in order to remove residual solvent. The ASD was dried for 24 h on the tray dryer. The residual amount of MeOH was less than 30 ppm determined by GC after the tray dryer.

Figure 27:
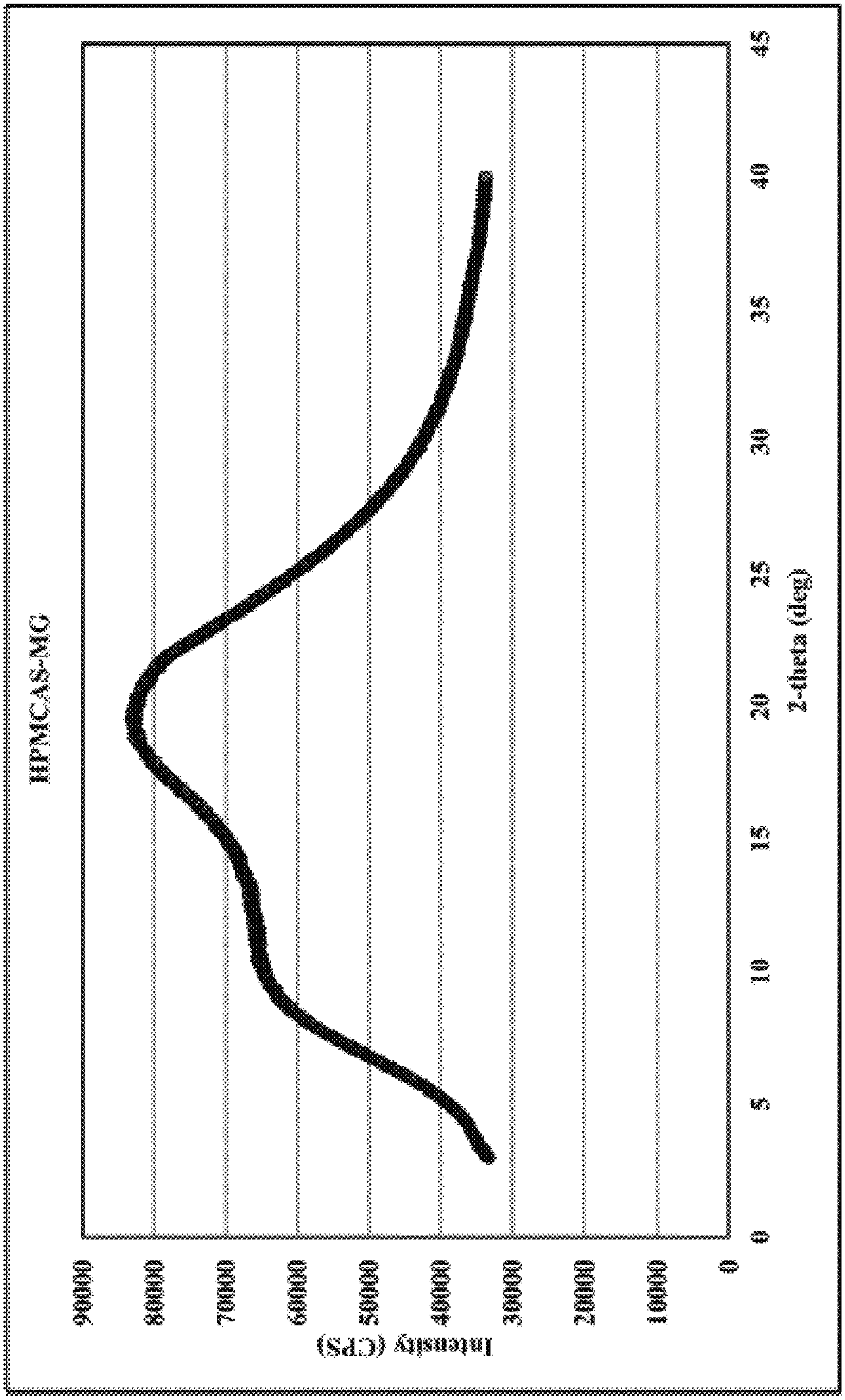
FIG. 27: PXRD of the ASD prepared according to example 9.

FIG. 27 shows the PXRD of the ASD after tray drying. The PXRD shows the ASD to be amorphous as indicated by the lack of sharp diffraction peaks.

Example 10: ASD Using MeOAc/MeOH Mixture—25:75 Gefitinib:HPMC E3

74.8 g of 40/40/20 (w/w/w) methanol/methyl acetate/water was weighed into a flask. 1.00 g of gefitinib was added to the mixed solvent and stirred with a magnetic stir bar at 24° C. until completely dissolved. 3.00 g of HPMC E3 was added, and the mixture was stirred for at least 30 min until the polymer was dissolved.

Then the solution was spray dried using a custom built spray dryer. The solution was pumped into a lab-scale 0.3 m diameter stainless steel spray drying chamber using head pressure on the tank of 120 psi. The spray solution was atomized using the nozzle:

1.5 pressure-swirl nozzle with 0.15 mm diameter; SCHLICK Hollow-Cone, model 121 with normal spray cone, Schlick Americas, Bluffton, South Carolina, USA.

Heated nitrogen gas (145 to 150° C. inlet, 48 to 53° C. outlet, 500 g/min) was used to dry the particles. The resulting ASD was collected using a cyclone to separate the solid particles from the gas stream.

The collected ASD was placed in a tray dryer at 40° C./15% RH for secondary drying in order to remove residual solvent. The ASD was dried for 24 h on the tray dryer. The residual amount of MeOH was less than 10 ppm determined by GC after the tray dryer.

Figure 28:
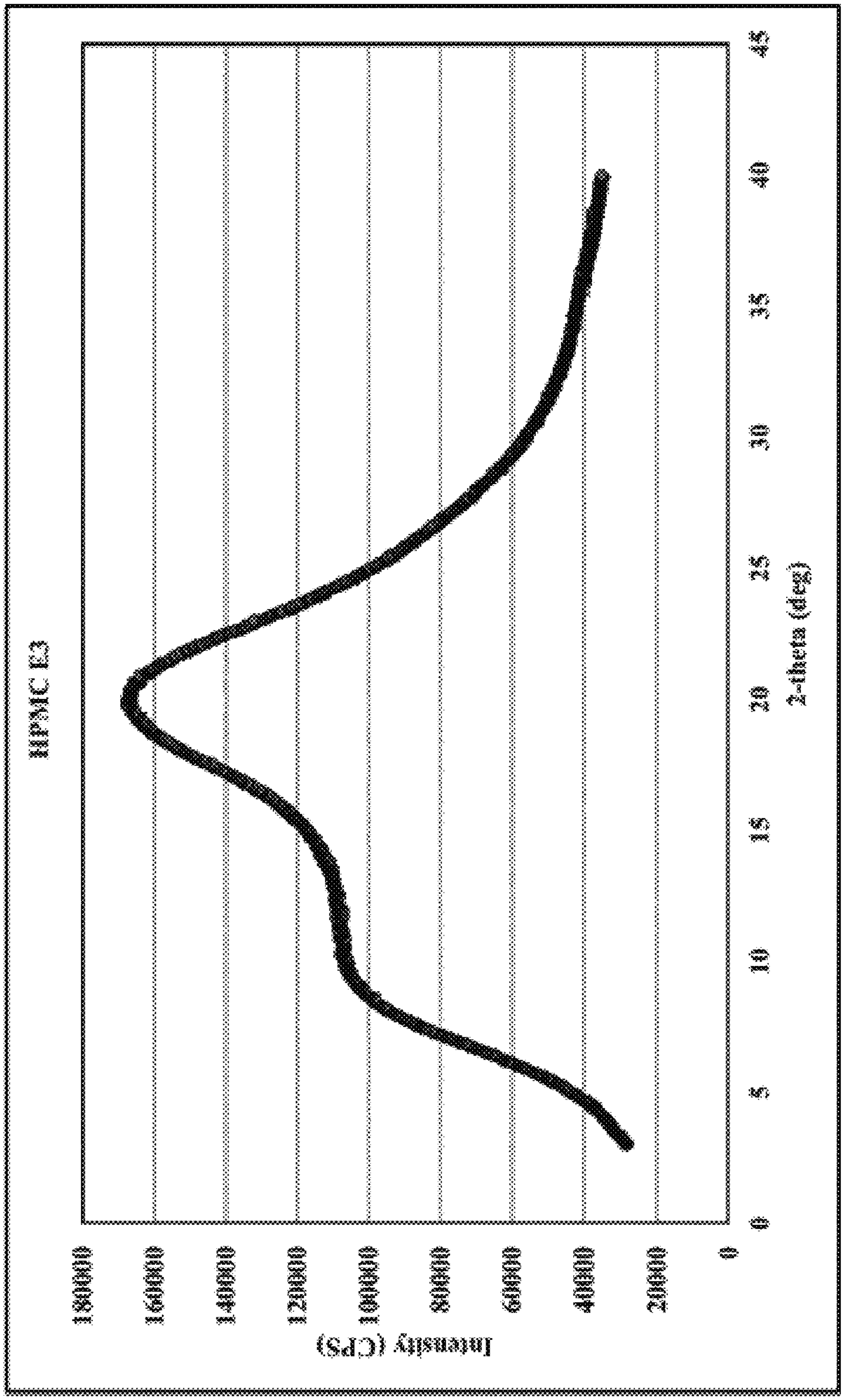
FIG. 28: PXRD of the ASD prepared according to example 10.

FIG. 28 shows the PXRD of the ASD after tray drying. The PXRD shows the ASD to be amorphous as indicated by the lack of sharp diffraction peaks.

Example 11: Solubilities Sulfasalazine in MeOAc:MeOH and EtOAc/MeOH

Table 11 shows the values of the solubility in wt %, the saturation concentration of Sulfasalazine in EtOAc/MeOH mixtures.

TABLE 11

| Sulfasalazine in EtOAc/MeOH | | |
|---|---|---|
| MeOH (wt %) | Solubility (wt %) | Std. Dev. (wt %) |
| 0 | 0.065 | 0.003 |
| 20 | 0.430 | 0.012 |
| 35 | 0.593 | 0.003 |
| 50 | 0.497 | 0.010 |
| 65 | 0.481 | 0.008 |
| 80 | 0.370 | 0.010 |
| 100 | 0.153 | 0.004 |

Table 12 shows the values of the solubility in wt %, the saturation concentration of Sulfasalazine in MeOAc/MeOH mixtures.

TABLE 12

| Sulfasalazine in MeOAc/MeOH | | |
|---|---|---|
| MeOH (wt %) | Solubility (wt %) | Std. Dev. (wt %) |
| 0 | 0.065 | 0.003 |
| 20 | 0.403 | 0.003 |
| 35 | 0.482 | 0.003 |
| 50 | 0.426 | 0.001 |
| 65 | 0.341 | 0.009 |
| 80 | 0.250 | 0.009 |
| 100 | 0.153 | 0.004 |

Figure 31:
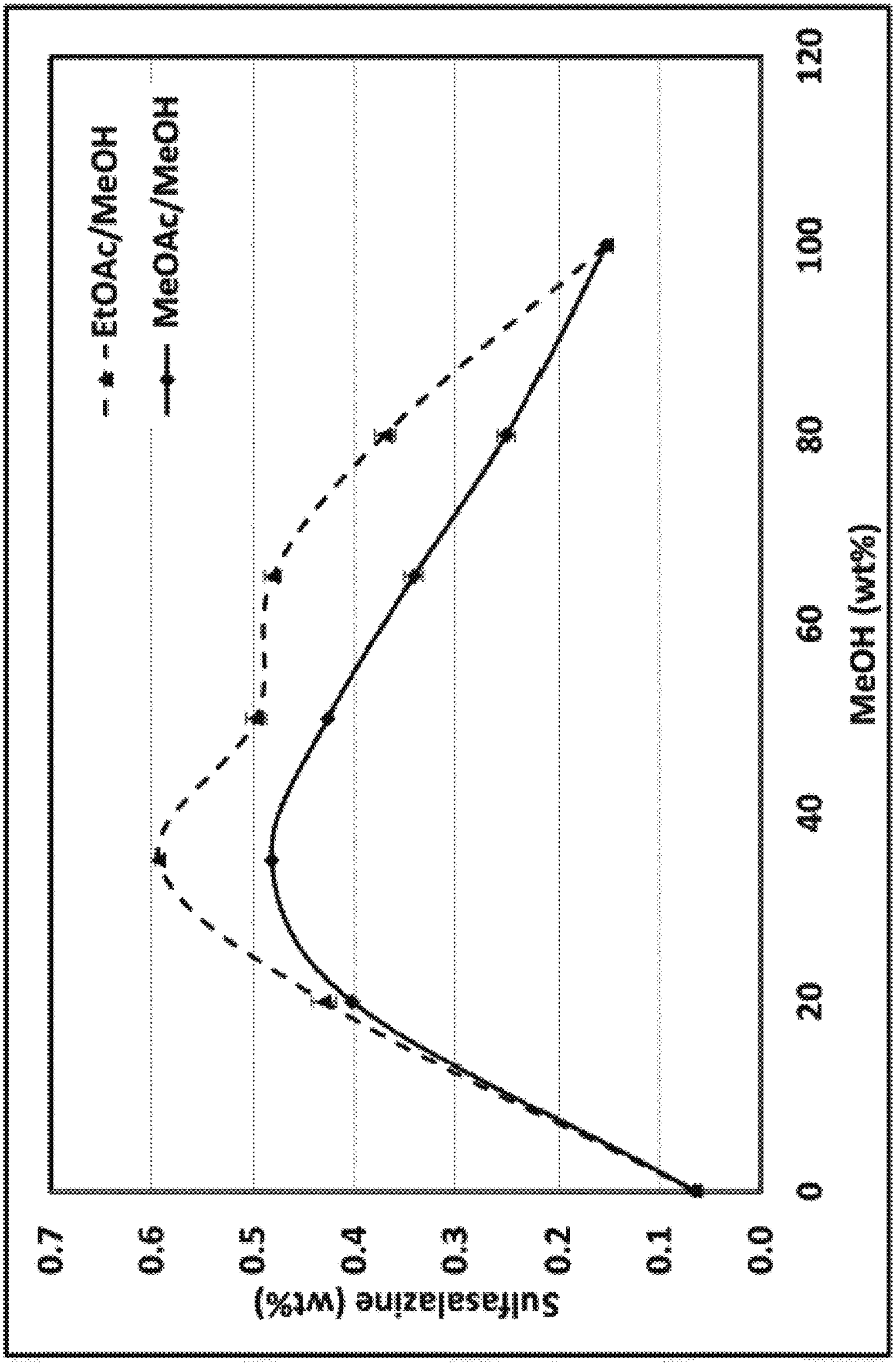
FIG. 31: Solubility in wt %, the saturation concentration of Sulfasalazine in EtOAc/MeOH and MeOAc/MeOH mixtures.

FIG. 31: shows an overlay of the solubility data of Table 11 and 12 in wt %, the saturation concentration of Sulfasalazine in EtOAc/MeOH and MeOAc/MeOH mixtures.

Example 12: Solubilities Nilotinib in MeOAc:MeOH and EtOAc/MeOH

Table 13 shows the values of the solubility in wt %, the saturation concentration of Nilotinib in EtOAc/MeOH mixtures.

TABLE 13

| Sulfasalazine in EtOAc/MeOH | | |
|---|---|---|
| MeOH (wt %) | Solubility (wt %) | Std. Dev. (wt %) |
| 0 | 0.091 | 0.003 |
| 15 | 0.500 | 0.004 |
| 30 | 0.847 | 0.010 |
| 45 | 1.028 | 0.002 |
| 60 | 0.878 | 0.003 |
| 85 | 0.532 | 0.008 |
| 100 | 0.371 | 0.003 |

Table 14 shows the values of the solubility in wt %, the saturation concentration of Nilotinib in MeOAc/MeOH mixtures.

TABLE 14

| Nilotinib in MeOAc/MeOH | | |
|---|---|---|
| MeOH (wt %) | Solubility (wt %) | Std. Dev. (wt %) |
| 0 | 0.091 | 0.003 |
| 15 | 0.496 | 0.001 |
| 30 | 0.763 | 0.009 |
| 45 | 0.962 | 0.001 |
| 60 | 0.868 | 0.007 |
| 85 | 0.486 | 0.002 |
| 100 | 0.371 | 0.003 |

Figure 32:
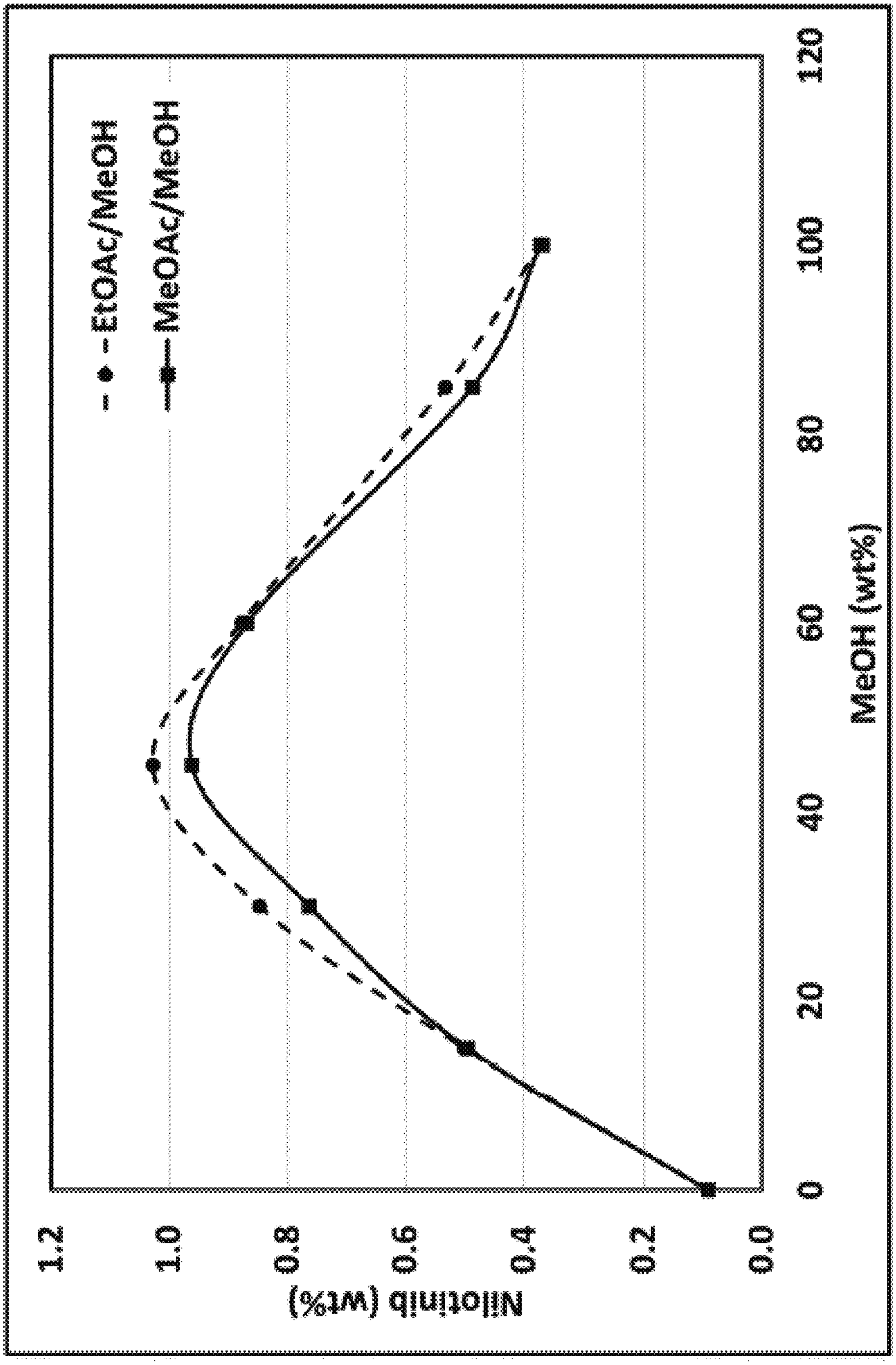
FIG. 32: Solubility in wt %, the saturation concentration of Nilotinib in EtOAc/MeOH and MeOAc/MeOH mixtures.

FIG. 32: shows an overlay of the solubility data of Table 13 and 14 in wt %, the saturation concentration of Nilotinib in EtOAc/MeOH and MeOAc/MeOH mixtures.

The invention claimed is:

1. A method for preparing an amorphous solid dispersion by spray drying a spray solution comprising:

a mixed solvent, the mixed solvent comprising i. a solvent 1 which is methyl acetate, and ii. a solvent 2 which is methanol, with the ratio (w:w) of solvent 1 to solvent 2 being from 10:90 to 90:10;

an active agent; and

HPMCAS as a dispersion polymer.

2. The method according to claim 1, wherein the spray solution has not more than one liquid phase.

3. The method according to claim 1, wherein the amount of mixed solvent in the liquid of the spray solution is at least 50 wt %, with the wt % being based on the weight of the liquid of the spray solution.

4. The method according to claim 1, wherein the active agent is a biologically active compound.

5. The method according to claim 1, wherein the amount of active agent in the spray solution is at least 0.5 wt %, with the wt % being based on the weight of the spray solution.

6. The method according to claim 1, wherein the concentration of the active agent dissolved in the mixed solvent is at least 1.1-fold higher than the solubility of the active agent in either solvent 1 or solvent 2 alone.

7. The method according to claim 1, wherein the ratio (w:w) of solvent 1: solvent 2 is from 20:80 to 80:20.

8. The method according to claim 1, wherein the combined amount of solvent 1 and solvent 2 in the mixed solvent is at least 70 wt %, with the wt % being based on the weight of the mixed solvent.

9. The method according to claim 1, wherein the mixed solvent further comprises water.

10. The method according to claim 9, wherein the mixed solvent comprises not more than 30 wt % of water, with the wt % being based on the weight of the mixed solvent.

11. The method according to claim 9, wherein the mixed solvent consists of a mixture of solvent 1, solvent 2, and water.

12. The method according to claim 1, wherein the mixed solvent consists of a mixture of solvent 1 and solvent 2.

* * * * *